(12) United States Patent
Yamakawa et al.

(10) Patent No.: US 11,099,141 B2
(45) Date of Patent: Aug. 24, 2021

(54) METHOD AND APPARATUS FOR PROCESSING PHOTON COUNTING-TYPE X-RAY DETECTION DATA AND X-RAY APPARATUS

(71) Applicant: JOB CORPORATION, Kanagawa (JP)

(72) Inventors: Tsutomu Yamakawa, Kanagawa (JP); Shuichiro Yamamoto, Kanagawa (JP); Masahiro Okada, Kanagawa (JP)

(73) Assignee: JOB Corporation, Kanagawa (JP)

( * ) Notice: Subject to any disclaimer, the term of this patent is extended or adjusted under 35 U.S.C. 154(b) by 0 days.

(21) Appl. No.: 16/627,451

(22) PCT Filed: Oct. 26, 2018

(86) PCT No.: PCT/JP2018/039884
§ 371 (c)(1),
(2) Date: Dec. 30, 2019

(87) PCT Pub. No.: WO2019/083014
PCT Pub. Date: May 2, 2019

(65) Prior Publication Data
US 2020/0249179 A1    Aug. 6, 2020

(30) Foreign Application Priority Data

Oct. 26, 2017 (JP) .............................. JP2017-207458

(51) Int. Cl.
*G01N 23/00* (2006.01)
*G01N 23/087* (2018.01)
(Continued)

(52) U.S. Cl.
CPC ......... *G01N 23/087* (2013.01); *A61B 6/4241* (2013.01); *G01N 23/04* (2013.01);
(Continued)

(58) Field of Classification Search
CPC .. A61B 6/00; A61B 6/4241; G01N 2223/206; G01N 2223/423; G01N 23/04; G01N 23/087; G01N 23/18; G01T 1/36
See application file for complete search history.

(56) References Cited

U.S. PATENT DOCUMENTS

2003/0072409 A1   4/2003  Kaufhold
2007/0237288 A1  10/2007  Tkaczyk et al.

FOREIGN PATENT DOCUMENTS

JP    2006-101926    4/2006
JP    2017-127638    7/2017
(Continued)

OTHER PUBLICATIONS

Kimoto, Natsumi et al., "Precise material identification ... effect in X-ray spectra", Applied Radiation and Isotopes, Mar. 9, 2017, vol. 124, pp. 16-26.
(Continued)

*Primary Examiner* — Dani Fox
(74) *Attorney, Agent, or Firm* — Carrier Blackman & Associates, P.C.; Joseph P. Carrier; William D. Blackman

(57) ABSTRACT

A higher accuracy beam hardening correction with a low calculation load is performed with objects whose elements have a wider range of effective atomic numbers $Z_{eff}$, thereby contributing to presentation of more quantitative X-ray images. Of two or more X-ray energy bins, two X-ray bins are selected to normalize X-ray attenuation amount μt in those bins such that one or more normalized X-ray attenuation amounts are obtained at each pixel areas. From reference information indicating a theoretical relationship of correspondence between the normalized X-ray attenuation amounts and effective atomic numbers of elements, one ore more effective atomic numbers are estimated every pixel area. Among the one or more effective atomic numbers ($Z_{High}$, $Z_{Low}$) and an effective atomic number (Zm) preset (Continued)

for the beam hardening correction, two or more atomic numbers are subjected to their equality determination.

28 Claims, 25 Drawing Sheets

(51) Int. Cl.
  *A61B 6/00* (2006.01)
  *G01N 23/04* (2018.01)
  *G01T 1/36* (2006.01)
(52) U.S. Cl.
  CPC .......... *G01T 1/36* (2013.01); *G01N 2223/206* (2013.01); *G01N 2223/423* (2013.01)

(56) References Cited

FOREIGN PATENT DOCUMENTS

| JP | 2017-528735 | 9/2017 |
| WO | 2010/061810 | 6/2010 |
| WO | 2016/171186 | 10/2016 |
| WO | 2017/069286 | 4/2017 |

OTHER PUBLICATIONS

Supplementary European Search Report issued in the corresponding European Patent Application No. 18 87 0980, received Jul. 7, 2021.

FIG.4
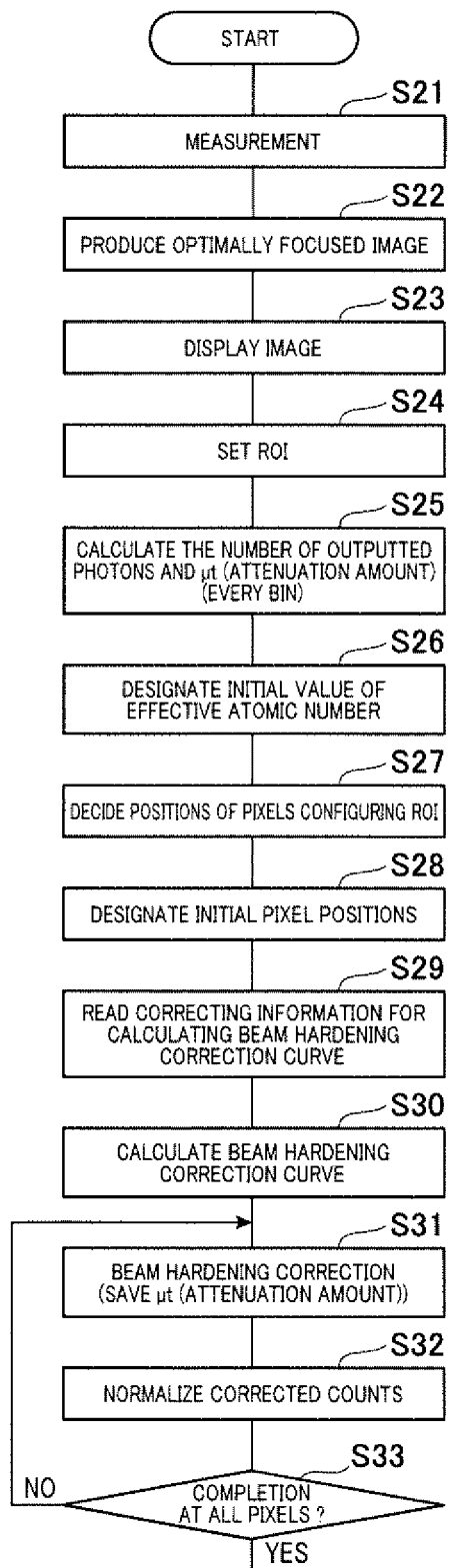
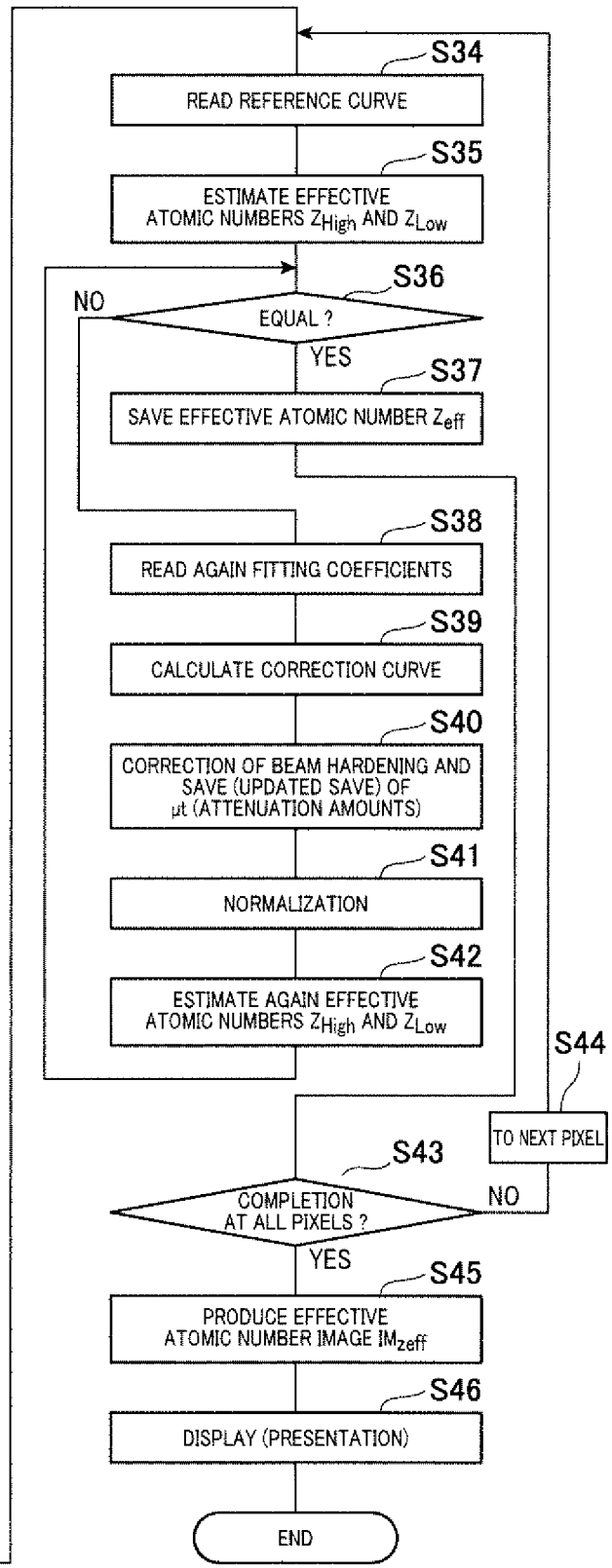

FIG.12

Fitting COEFFICIENTS FOR EACH $a_j$ (A) [LOWER ENERGY BIN : $Bin_{Low}$]

| | $a_0(Z)$ | $a_1(Z)$ | $a_2(Z)$ | $a_3(Z)$ | $a_4(Z)$ |
|---|---|---|---|---|---|
| $M_0$ | 1.3974.E+00 | 4.0452.E-01 | -8.2425.E-03 | -4.2203.E-04 | 1.4314.E-05 |
| $M_1$ | ×××××× | ××××× | ×××××× | ×××××× | ×××× |
| $M_2$ | ×××××× | ××××× | ×××××× | ×××××× | ×××× |
| $M_3$ | ×××××× | ××××× | ×××××× | ×××××× | ×××× |
| $M_4$ | ×××××× | ××××× | ×××××× | ×××××× | ×××× |

(B) [MIDDLE ENERGY BIN : $Bin_{Middle}$]

| | $a_0$ | $a_1$ | $a_2$ | $a_3$ | $a_4$ |
|---|---|---|---|---|---|
| $M_0$ | 1.0376.E+00 | -9.1946.E-02 | 1.2129.E-02 | -4.7470.E-04 | 6.2999.E-06 |
| $M_1$ | ×××××× | ××××× | ×××××× | ×××××× | ×××× |
| $M_2$ | ×××××× | ××××× | ×××××× | ×××××× | ×××× |
| $M_3$ | ×××××× | ××××× | ×××××× | ×××××× | ×××× |
| $M_4$ | ×××××× | ××××× | ×××××× | ×××××× | ×××× |

(C) [HIGHER ENERGY BIN : $Bin_{High}$]

| | $a_0$ | $a_1$ | $a_2$ | $a_3$ | $a_4$ |
|---|---|---|---|---|---|
| $M_0$ | 1.0041.E+00 | -2.4476.E-02 | -1.1843.E-03 | 1.3481.E-04 | -2.8081.E-06 |
| $M_1$ | ×××××× | ××××× | ×××××× | ×××××× | ×××× |
| $M_2$ | ×××××× | ××××× | ×××××× | ×××××× | ×××× |
| $M_3$ | ×××××× | ××××× | ×××××× | ×××××× | ×××× |
| $M_4$ | ×××××× | ××××× | ×××××× | ×××××× | ×××× |

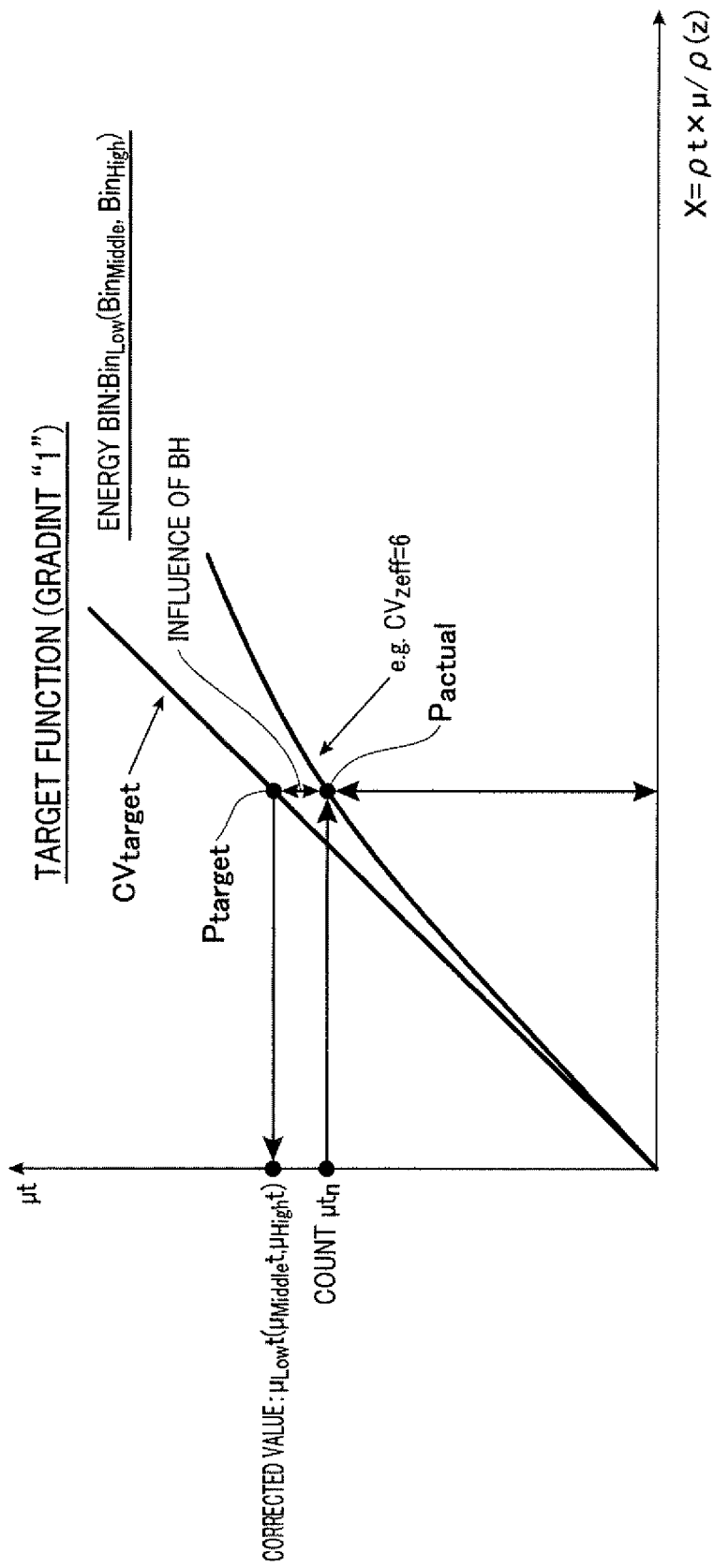

| PIXEL POSITION | BEAM-HARDENING CORRECTED ATTENUATION AMOUNT (FOR EACH ENERGY BIN) | | | NORMALIZED ATTENUATION AMOUNT | | EFFECTIVE ATOMIC NUMBER | | |
|---|---|---|---|---|---|---|---|---|
| | (LOW) $Bin_{Low}$ | (MIDDLE) $Bin_{Middle}$ | (HIGH) $Bin_{High}$ | LOWER SIDE | HIGHER SIDE | $Z_{Low}$ | $Z_{High}$ | $Z_{eff}$ |
| 1 | $\mu_{Low}t(1)$ | $\mu_{Middle}t(1)$ | $\mu_{High}t(1)$ | | | | | |
| 2 | $\mu_{Low}t(2)$ | $\mu_{Middle}t(2)$ | $\mu_{High}t(2)$ | | | | | |
| 3 | $\mu_{Low}t(3)$ | $\mu_{Middle}t(3)$ | $\mu_{High}t(3)$ | | | | | |
| ⋮ | | | | | | | | |
| n | $\mu_{Low}t(n)$ | $\mu_{Middle}t(n)$ | $\mu_{High}t(n)$ | | | | | |

⇓ 36

(B)

| PIXEL POSITION | BEAM-HARDENING CORRECTED ATTENUATION AMOUNT (FOR EACH ENERGY BIN) | | | NORMALIZED ATTENUATION AMOUNT | | EFFECTIVE ATOMIC NUMBER | | |
|---|---|---|---|---|---|---|---|---|
| | (LOW) $Bin_{Low}$ | (MIDDLE) $Bin_{Middle}$ | (HIGH) $Bin_{High}$ | LOWER SIDE | HIGHER SIDE | $Z_{Low}$ | $Z_{High}$ | $Z_{eff}$ |
| 1 | $\mu_{Low}t(1)$ | $\mu_{Middle}t(1)$ | $\mu_{High}t(1)$ | $\mu_{Low-nor}(1)$ | $\mu_{High-nor}(1)$ | | | |
| 2 | $\mu_{Low}t(2)$ | $\mu_{Middle}t(2)$ | $\mu_{High}t(2)$ | $\mu_{Low-nor}(2)$ | $\mu_{High-nor}(2)$ | | | |
| 3 | $\mu_{Low}t(3)$ | $\mu_{Middle}t(3)$ | $\mu_{High}t(3)$ | $\mu_{Low-nor}(3)$ | $\mu_{High-nor}(3)$ | | | |
| ⋮ | | | | | | | | |
| n | $\mu_{Low}t(n)$ | $\mu_{Middle}t(n)$ | $\mu_{High}t(n)$ | $\mu_{Low-nor}(n)$ | $\mu_{High-nor}(n)$ | | | |

⇓ 36

(C)

| PIXEL POSITION | BEAM-HARDENING CORRECTED ATTENUATION AMOUNT (FOR EACH ENERGY BIN) | | | NORMALIZED ATTENUATION AMOUNT | | EFFECTIVE ATOMIC NUMBER | | |
|---|---|---|---|---|---|---|---|---|
| | (LOW) $Bin_{Low}$ | (MIDDLE) $Bin_{Middle}$ | (HIGH) $Bin_{High}$ | LOWER SIDE | HIGHER SIDE | $Z_{Low}$ | $Z_{High}$ | $Z_{eff}$ |
| 1 | $\mu_{Low}t(1)$ | $\mu_{Middle}t(1)$ | $\mu_{High}t(1)$ | $\mu_{Low-nor}(1)$ | $\mu_{High-nor}(1)$ | $Z_{Low}(1)$ | $Z_{High}(1)$ | |
| 2 | $\mu_{Low}t(2)$ | $\mu_{Middle}t(2)$ | $\mu_{High}t(2)$ | $\mu_{Low-nor}(2)$ | $\mu_{High-nor}(2)$ | $Z_{Low}(2)$ | $Z_{High}(2)$ | |
| 3 | $\mu_{Low}t(3)$ | $\mu_{Middle}t(3)$ | $\mu_{High}t(3)$ | $\mu_{Low-nor}(3)$ | $\mu_{High-nor}(3)$ | $Z_{Low}(3)$ | $Z_{High}(3)$ | |
| ⋮ | | | | | | | | |
| n | $\mu_{Low}t(n)$ | $\mu_{Middle}t(n)$ | $\mu_{High}t(n)$ | $\mu_{Low-nor}(n)$ | $\mu_{High-nor}(n)$ | $Z_{Low}(n)$ | $Z_{High}(n)$ | |

⇓ 36

(D)

| PIXEL POSITION | BEAM-HARDENING CORRECTED ATTENUATION AMOUNT (FOR EACH ENERGY BIN) | | | NORMALIZED ATTENUATION AMOUNT | | EFFECTIVE ATOMIC NUMBER | | |
|---|---|---|---|---|---|---|---|---|
| | (LOW) $Bin_{Low}$ | (MIDDLE) $Bin_{Middle}$ | (HIGH) $Bin_{High}$ | LOWER SIDE | HIGHER SIDE | $Z_{Low}$ | $Z_{High}$ | $Z_{eff}$ |
| 1 | $\mu_{Low}t(1)$ | $\mu_{Middle}t(1)$ | $\mu_{High}t(1)$ | $\mu_{Low-nor}(1)$ | $\mu_{High-nor}(1)$ | $Z_{Low}(1)$ | $Z_{High}(1)$ | $Z_{eff}(1)$ |
| 2 | $\mu_{Low}t(2)$ | $\mu_{Middle}t(2)$ | $\mu_{High}t(2)$ | $\mu_{Low-nor}(2)$ | $\mu_{High-nor}(2)$ | $Z_{Low}(2)$ | $Z_{High}(2)$ | $Z_{eff}(2)$ |
| 3 | $\mu_{Low}t(3)$ | $\mu_{Middle}t(3)$ | $\mu_{High}t(3)$ | $\mu_{Low-nor}(3)$ | $\mu_{High-nor}(3)$ | $Z_{Low}(3)$ | $Z_{High}(3)$ | $Z_{eff}(3)$ |
| ⋮ | | | | | | | | |
| n | $\mu_{Low}t(n)$ | $\mu_{Middle}t(n)$ | $\mu_{High}t(n)$ | $\mu_{Low-nor}(n)$ | $\mu_{High-nor}(n)$ | $Z_{Low}(n)$ | $Z_{High}(n)$ | $Z_{eff}(n)$ |

ESTIMATION OF EFFECTIVE ATOMIC NUMBER (IDENTIFICATION OF SUBSTANCE)

FIG.21

| PIXEL No. | ENERGY BIN | BEAM-HARDENING CORRECTED FINAL μt (ATTENTION AMOUNT) |
|---|---|---|
| 1 | $Bin_{Low}$ | $\mu_{Low}t(1)$ |
| 1 | $Bin_{Middle}$ | $\mu_{Middle}t(1)$ |
| 1 | $Bin_{Hign}$ | $\mu_{Hight}(1)$ |
| 2 | $Bin_{Low}$ | $\mu_{Low}t(2)$ |
| 2 | $Bin_{Middle}$ | $\mu_{Middle}t(2)$ |
| 2 | $Bin_{Hign}$ | $\mu_{Hight}(2)$ |

[3D SCATTER DIAGRAM]

[ABSORPTION VECTOR LENGTH IMAGE]

METHOD AND APPARATUS FOR PROCESSING PHOTON COUNTING-TYPE X-RAY DETECTION DATA AND X-RAY APPARATUS

TECHNICAL FIELD

The present invention relates to a method and an apparatus for processing detection data of X-rays which have been transmitted through an object and an X-ray apparatus, and in particular, to a method and an apparatus for processing data acquired by radiating to an object X-rays having a continuous spectrum and detecting the X-rays in a photon counting manner and a photon counting X-ray apparatus.

BACKGROUND ART

In recent years, inspection using X-ray beams to check the internal state of an object has been widely used in various fields, such as foreign matter inspection of food, baggage inspection, and medical X-ray mammography.

For example, there is proposed a technique as set forth in a patent publication 1 (JP-A-2010-091483, title of the invention is a "method and apparatus for inspecting foreign matters"). This patent publication 1 is based on an inspection technique called a dual energy technique (or a subtraction technique). This inspection technique uses the fact that two types of X-rays of energy (that is, two types of X-rays having different wavelengths) penetrating a substance arises a difference therebetween in X-ray transmission information. Practically, this inspection technique uses the following processing. First, two types of X-ray images based on lower X-ray energy and higher X-ray energy are made simultaneously, and a difference between the images is calculated. Then, from the resultant image difference, image components of a mingled foreign matter are extracted. The image components are then subjected to threshold processing to detect the foreign matter.

By the way, when radiated beam-formed X-rays are transmitted through an object, there is caused a beam hardening phenomenon in the X-rays during the transmission. This phenomenon is caused due to the fact that, when polychromatic X-rays are radiated to a substance, lower X-ray energy components are likely to be absorbed in the substance more than higher X-ray energy components so that components of the X-rays that have been transmitted are shifted in their ratios toward a higher X-ray energy side. When this phenomenon is caused, an effective energy amount is also shifted to the higher energy side.

The beam hardening phenomenon, which is unavoidable in X-ray apparatuses, is described for example in patent publications 1 and 2. The patent publication 1 exemplifies an X-rat apparatus provided with an X-ray generator generating to an object pulsed beam-formed X-rays having a continuous spectrum (i.e., polychromatic spectrum) and a photon counting detector. The detector detects the X-rays which have been transmitted through the object as a flow of photons, and outputs electric signals depending on energy of the photons. For this reason, this X-ray apparatus adopts a process which reconstructs an image with less artifact caused due to the beam hardening phenomenon.

In addition, in the patent publication 2 provides an X-ray apparatus equipped with an X-ray source and an X-ray detector, a process is exemplified which corrects influence of the beam hardening phenomenon with signals detected by the detector. By this process, a plurality of projection data are produced with different thickness of phantoms, the projection data are plotted in a graph every transmission distances of the X-rays in an object, and the plotted data and their theoretical values are related to each other to make a beam hardening correction function. Hence, by way of example, to reduce influence of the beam hardening phenomenon, it is conceivable of a configuration in which the radiation detecting apparatus disclosed in the patent publication 1 produces the correction function disclosed in the patent publication 2 and the produced correction function is used to correct measurements of the beam-formed X-rays which have been transmitted through an object.

In addition, it is known that the beam hardening correction can be performed with use of two reference substances consisting of iodine and water in CT apparatuses which are called monochromic CT apparatuses.

CITATION LIST

Patent References

[Patent Publication 1] JP 2006-101926 A
[Patent Publication 2] WO 2010/061810 A
[Patent Publication 3] WO 2016/171186 A
[Patent Publication 4] WO 2017/069286 A

SUMMARY OF THE INVENTION

Technical Problem

However, although using the correction functions, the beam hardening correction technique disclosed by the patent publication 2 is confronted with a difficulty that a one correction function covers only a very narrow range of effective atomic numbers of objects. Herein, the effective atomic number Zeff is an average atomic number averaging a plurality of types of atomic numbers of elements (substances) which are present in the X-ray beam paths in the object. Hence, in the patent publication 2, the correction technique may be decided to use a reference substance (for example, nitrogen N having an atomic number Z=7). Based on this reference, the correction function may be decided. In such a case, however, in an actual application, an application range to which the correction function cab be applied is narrow, that is, a range which assures a specified precision for the correction is narrow, at most, the range is Z=±2. In other words, the range which is able to suppress the influence of the beam hardening phenomenon effectively into an allowable range using the correction function is narrower such as Z=±2.

In practice, in performing X-ray mammography imaging, there are present various types of substances such as fat, mammary gland, etc. in the X-ray beam paths. Such substances have atomic numbers 6 to 7. However, in the dental field in which X-ray tomographic dental imaging is carried out, the radiated X-rays usually encounter both hard and soft tissues, so that this means that a range of atomic numbers which should be covered for a proper beam hardening correction is wider.

In this way, in the X-ray imaging, the conventional beam hardening correction cannot cope with many types of substances using only one correction function. In addition, as stated, in the CT apparatuses called monochromatic CT apparatuses, when two substances such as iodine and water are representatively given atomic numbers Z1 and Z2 and the bean hardening correction is carried out with such atomic numbers, an appropriate precision in the correction is not guaranteed outside in ranges other than Z1+/−2, and Z2+/−2.

Furthermore, a degree at which the beam hardening phenomenon occurs changes depending on both a thickness t of on an object through which the X-rays pass and amounts of such X-ray energy amounts. Hence, even if the beam hardening correction may be carried out in an expedient manner in such cases as some kinds of simple experiments or estimation on substances having such a narrow range, it is very difficult to obtain detailed and precise corrected information.

In recent years, the present investors have already developed a technique of identifying (determining, estimating, or evaluating) changes in the type or states of substances which are present in the X-ray paths. This technique uses a photon counting X-ray detector, in which a plurality of bins (energy ranges) are set in a continuous X-ray spectrum, photon counts (counted values) are collected in each of the energy bins, and these collected data are subjected to the identification with no dependency on a thickness t of the object (i.e., the length of the X-ray path in the object). As a general term, this technique has been referred by the inventors as substance identification. In perming the substance identification, it should be considered that actual applications (medical diagnosis, foreign-matter inspection, etc.) require what range of atomic numbers in relation to subjects to be examined in the X-ray detection (in this respect, refer to the patent publication 3).

In this performing the sustenance identification in a higher accuracy, a beam hardening correction technique is required, all the more, in a higher accuracy manner. With consideration of this issue, in the correction proposed by the patent publication 4 proposed by the inventors, the characteristic based on an X-ray attenuation amount μt which is defined, before the corrosion, by both known thicknesses t which are mutually different in the X-ray path directions in a subject and corresponding X-ray attenuation amounts μt, based on the counts from the photon counting detector, every X-ray energy bin. This subject is a reference subject, which composes an object being imaged or inspected. The subject should be the same (or the same kind) as that should be inspected or should be composed of elements which are regarded as being like the elements in terms of their atomic members. In a two-dimensional coordinate whose horizontal axis is assigned to the thicknesses t and whose vertical axis is assigned to X-ray attenuation amounts μt provided before the correction, correcting data are calculated for replacing the mapped data by data along a linear target characteristic passing throaty the origin of the coordinate. The correcting data are calculated very X-ray energy bin. Using such correcting data, every energy bin and if necessary, every pixel, the actual counts, that is, the X-ray attenuation amounts μt provided before the correction are then corrected.

This conventional correction is still useful in improving a difficulty that beam hardened amounts depend on amounts of X-ray energy amounts, since a plurality of pixels composing an imaging are now targeted are processed every energy bin. However, although the linear target characteristic is provided based on the reference substance (such as nitrogen having an atomic number N=7), a range for proper beam hardening correction using such reference substance is actually $Z_{eff}=\pm 2$ in terms of the effective atomic number $Z_{eff}$, which is still narrow for various types of substances necessary for actual applications.

With consideration of such situations, as seen in imaging human bodies or human jaws for medical analyses, there are applications which need to image objects having a wider range of effective atomic numbers $Z_{eff}$. In such cases, there is still a room for more improving performance of the beam hardening correction with higher precision.

As one improvement measure, there should prepare a plurality of target characteristics assigned receptively to a plurality of types of objects, with selecting a desired one when in correcting. However, it is not known that an object being inspected is covered by the plurality of target characteristics prepared in advance. Hence, every time when the inspection is carried out, the target characteristic should be selected, which is hard to the doctor and the calculation unit in the apparatus in interpreting images.

<Object of the Invention>

The present invention is thus provided to be applied to X-ray photon counting directed to measurement of substances having elements whose range of effective atomic numbers Zeff is wider, to be able to perform the beam hardening correction of the counts with less calculation load and with higher precision, and to be able to present various modes of qualitative image information and/or higher-precision information about substance identification based on the X-ray attenuation amounts subjected to the beam hardening correction. The present invention having above objects is directed to an apparatus and a method of realizing the above objects and an X-ray apparatus.

Solution to the Problems

In order to accomplish the foregoing object, there is provided a one mode of the present invention providing a method of processing data of count values, the count values being provided by radiating beam-formed X-rays having a continuous X-ray spectrum to an object, detecting the X-rays transmitted through the object, and counting, as the count values, photons of the X-rays in each of two or more preset X-ray energy bins and in each of pixel areas each consisting of one or more pixels.

This method is characterized to include:

a calculation step calculating, in each of the X-ray energy bins and at each of the pixel areas, count data indicated by a ratio between the count values obtained with no object and with the object;

a correction step performing beam hardening correction with the count data at each of the pixel areas and in each of the X-ray energy bins to obtain X-ray attenuation amounts ($\mu_{Low}t$, $\mu_{Middle}t$, $\mu_{High}t$) (μt: μ denotes a linear attenuation coefficient and t denotes a thickness of the object in a projection direction of the X-rays in the object), based on correcting information according to a preset effective atomic number, the beam hardening correction correcting a beam hardening phenomenon caused when the X-rays are transmitted through the object;

a normalization step normalizing, of the three or more X-ray energy bins, X-ray attenuation amounts ($\mu_{Low}t$, $\mu_{Middle}t$) in two energy bins on a lower energy side to obtain normalized X-ray attenuation amounts (($\mu_{Low}/(\mu_{Low}^2+\mu_{Middle}^2)^{1/2}$) on the lower energy side and X-ray attenuation amounts ($\mu_{Middle}t$, $\mu_{High}t$) in two energy bins on a higher energy side to obtain normalized X-ray attenuation amounts (($\mu_{High}/(\mu_{Middle}^2+\mu_{High}^2)^{1/2}$) on the higher energy side, at each of the pixel areas;

an estimation step estimating, from reference information showing a theoretical relationship between the normalized X-ray attenuation amounts and effective atomic numbers of elements, an effective atomic number ($Z_{Low}$) on the lower energy side and an effective atomic number ($Z_{High}$) on the higher energy side corresponding, respectively, to the normalized X-ray attenuation amounts ($\mu_{Low}/(\mu_{Low}^2 + \mu_{Middle}^2)^{1/2}$) on the lower energy side and the normalized X-ray attenuation amounts ($\mu_{High}/(\mu_{Middle}^2 + \mu_{High}^2)^{1/2}$) on the lower energy side, at each of the pixel area;

an equality determining step determining whether or not the effective atomic number ($Z_{Low}$) on the lower energy side and the effective atomic number ($Z_{High}$) on the higher energy side are equal to each other or regarded as being equal to each other. A processing apparatus which performs processing equivale to the foregoing steps is also provided.

Particularly, the preprocessing step includes:

a step setting a desired range (Zmin to Zmax) of effective atomic numbers of elements composing compositions of the object;

a step theoretically estimating a graph of respective effective atomic numbers in a two-dimensional coordinate having a horizontal axis and a vertical axis, wherein the horizontal axis is assigned to a mass thickness ($\rho t$) of an element and the vertical axis is assigned to a linear attenuation amount ($\mu t$: $\mu$ denotes a linear attenuation coefficient of the element, t denotes a thickness of the object in an X-ray path direction) at an effective energy amount in each of the X-ray energy bins, the element having a plurality of effective atomic numbers (for example, Z=5 to 14) selected discretely from an effective atomic number (Zm) in the desired range of the effective atomic numbers, the plurality of effective atomic numbers (for example, Z=5 to 14) including a lower limit and an upper limit of the desired range;

a step designating a desired effective atomic number (for example, Zm=7) from the effective atomic numbers belonging to the desired range (Zmin to Zmax);

a step setting a linear target ruction in the two-dimensional coordinate when assuming that monochromatic X-rays are radiated to the object composed of the element having the designated effective atomic number (for example, Zm=7);

a step generalizing, in the two-dimensional coordinate, by multiplying the horizontal axis direction by a gradient ($\mu/\rho$) of the target function to generalize a plurality of curves provided by the plurality of effective atomic numbers (for example, Z=5 to 14) as a variable of the effective atomic numbers; and a step designating a curve of the element having the designated effective atomic number (for example, Zm=7) among the plurality of generalized curves, and, before correcting the beam hardening, saves, into a storage, beam hardening correction functions as the correcting information based on residual errors between the designated curve and the other curves, the beam hardening correction functions being for correcting the beam hardening.

In order to accomplish the foregoing object, there is also provided a processing method according to a second mode of the present invention. This processing method processes data of count values, the count values being provided by radiating beam-formed X-rays having a continuous X-ray spectrum to an object, detecting the X-rays transmitted through the object, and counting, as the count values, photons of the X-rays in each of two or more preset X-ray energy bins and in each of pixel areas each consisting of one or more pixels.

The method includes a preprocessing step previously preparing, for each of the X-ray energy bins, correcting information based on characteristics showing i) both mass thicknesses pt of a plurality of types of substances whose atomic numbers are known and ii) an X-ray attenuation amount $\mu t$ ($\mu$: a linear attenuation coefficient and t: a thickness of the object in an X-ray path direction passing through the object) at an effective energy among in each of the X-ray energy bins, the correcting information being for correcting X-ray count values subjected to a beam hardening pheromone when the X-rays are transmitted through the object; and an attenuation amount processing step processing by applying the correcting information, prepared by the preprocessing step, to the X-ray count values for the beam hardening correction at each of the pixel areas to finally decide the X-ray attenuation amounts and processing the decided X-ray attenuation amounts.

Moreover, there is provided an X-ray apparatus according to a third mode of the present invention. The X-ray apparatus processes data of count values, the count values being provided by radiating beam-formed X-rays having a continuous X-ray spectrum to an object, detecting the X-rays transmitted through the object, and counting, as the count values, photons of the X-rays in each of two or more preset X-ray energy bins and in each of pixel areas each consisting of one or more pixels.

This processing apparatus includes preprocessing means previously preparing, for each of the X-ray energy bins, correcting information based on characteristics showing i) both mass thicknesses pt of a plurality of types of substances whose atomic numbers are known and ii) an X-ray attenuation amount $\mu t$ ($\mu$: a linear attenuation coefficient and t: a thickness of the object in an X-ray path direction passing through the object) at an effective energy among in each of the X-ray energy bins, the correcting information being for correcting X-ray count values subjected to a beam hardening pheromone when the X-rays are transmitted through the object; and attenuation amount processing means processing by applying the correcting information, prepared by the preprocessing means, to the X-ray count values for the beam hardening correction at each of the pixel areas to finally decide the X-ray attenuation amounts and processing the decided X-ray attenuation amounts.

For example, the attenuation amount processing means includes X-ray image producing means producing a photon counting X-ray image based on the X-ray attenuation amounts corrected and finally decided by the correction means; and X-ray image presenting means presenting the produced X-ray image.

As a preferred example, the X-ray apparatus is an X-ray medical diagnosis apparatus or an X-ray non-destructive inspection apparatus, both of which is provided with a configuration of detecting the X-rays in a photon counting system.

Effect of the Invention

In the one mode of the present invention, in a desired range of effective atomic numbers (Zmin~Zmax), a desired effective atomic number (for example, Zm=7) is designated. A linear target function is set in the two-dimensional coordinate, which is provided when it is assumed that monochromatic X-rays are radiated to an object composed of an element having the designated effective atomic number (for example, Zm=7). In the two-dimensional coordinate, amounts along the horizontal axis direction are multiplied by a gradient of the target function, whereby a plurality of curves depicted respectively by the plurality of effective atomic numbers (for example, Z=5 to 14) are generalized using the effective atomic numbers as a variable. Among these generalized plural curves, a curve of the element having the designated effective number (for example, Zm=7) is designated. Based on residual errors between this designated effective atomic number (for example, Zm=7) and the other curves, a beam hardening correction function is saved as the correction information in a storage, before correcting the beam hardening using the beam hardening correction function.

For this reason, provided that the generalized target functions and information showing the residual errors for an effective atomic number designated in a preset range of effective atomic numbers are provided, the beam hardening correction functions can be calculated according to the foregoing procedures. This means that, even when a wider range of preset effective atomic numbers is employed, an amount of calculation can be less than that proportional to calculation of the beam hardening correction function. In other words, objects whose elements have a wider range of effective atomic numbers Zeff can be subjected to the beam hardening correction with less calculation load.

In another mode of the present invention, of the three or more X-ray energy bins, X-ray attenuation amounts ($\mu_{Low}t$, $\mu_{Middle}t$) in two energy bins on a lower energy side are normalized to obtain normalized X-ray attenuation amounts ($\mu_{Low}/(\mu_{Low}^2+\mu_{Middle}^2)^{1/2}$), while X-ray attenuation amounts ($\mu_{Middle}t$, $\mu_{High}t$) in two energy bins on a high energy side are normalized to obtain normalized X-ray attenuation amounts (($\mu_{High}/(\mu_{Middle}^2+\mu_{High}^2)^{1/2}$), at each of the pixel areas (each being composed of one pixel or a plurality of pixels).

Based on reference information showing a theoretical correspondence information between those normalized X-ray attenuation amounts and effective atomic numbers of elements, an effective atomic number ($Z_{Low}$) on the lower energy side and an effective atomic number ($Z_{High}$) on the higher energy side, respectively, corresponding to the normalized X-ray attenuation amount ($\mu_{Low}/(\mu_{Low}^2+\mu_{Middle}^2)^{1/2}$) on the lower energy side and the normalized X-ray attenuation amount ($\mu_{High}/(\mu_{Middle}^2+\mu_{High}^2)^{1/2}$) on the higher energy side are calculated, at each of the pixel areas.

Both the effective atomic numbers ($Z_{Low}$, $Z_{High}$) on the lower and higher energy sides are compared with each other in order to determine how an equality degree therebetween is. When this equality degree determination reveals that both numbers are equal or to be regarded as being equal, the effective atomic number showing the equality is decided as a formal effective atomic number.

In this way, based on the previously prepared reference information, the effective atomic numbers ($Z_{Low}$, $Z_{High}$) estimated from the lower and higher energy sides are used to search for an effective atomic number which can be regarded as a true value or a value close thereto. Hence, an effective atomic number image of a substance can be produced with higher precision. This results in more reliable identification of types of states, also expressed as properties, natures, or characteristics, of substances which are present in the X-ray transmission paths in an object.

Namely, according to the present invention, theoretical attenuation characteristics v.s. polychromatic X-rays of elements having various atomic numbers are generalized using, as a parameter, the effective atomic numbers Z. Among such theoretical attenuation characteristics, an attenuation characteristic is designated so that the designated attenuation characteristic has residual errors to the other attenuation characteristics. Information showing the residual errors is thus held as residual error information. These steps belong to a based preprocess of the whole data processing. In addition, correction information obtained by the preprocess is used to apply the beam hardening correction to actually acquired data at each of the pixel areas and for each of the energy bins, so that beam-hardening corrected vales (data) can be obtained. The beam-hardening corrected values are then provided to estimation of effective atomic numbers on the lower and higher energy sides. This estimation calculation is repeated until an effective atomic number becomes a true number or a number which can be regarded as an almost true number.

In this way, the correction information for the beam hardening correction which covers almost all effective atomic numbers necessary in usual medial applications can be obtained and saved relatively easily, in which a wide range of effective atomic numbers $Z_{eff}$ can be given by way of example (in an embodiment, Zmin to Zmax is Z=5 to 14).

This correction information can be utilized in clinical applications once being acquired, as long as a desired atomic number falls into the range. That is, it is very few that the correction information does not match an intended effective atomic number, whereby the correction information has broad utility. It is not necessary to frequently acquire correction information in accordance with an intended clinical application, as in the conventional cases.

In addition, in actual usage, it is sufficient that the correction information is given as fitting coefficients of residual error functions compensating the foregoing residual errors, in accordance with the effective atomic numbers $Z_{eff}$.

Therefore, compared with a correction scheme which needs many beam hardening correction functions to be prepared every characteristic thereof, a capacity of a storage which saves therein the correction information can be smaller. Hence, with covering a wider range of effective atomic numbers Zeff of intended substances, the beam hardening correction functions can be calculated more easily, in which the effective atomic numbers $Z_{eff}$ on the lower and higher energy sides are calculated in their equality. It is therefore possible to perform the beam hardening correction with higher precision compared with the conventional correction techniques.

In other words, to estimate a high-precision effective atomic number Zeff results in searching a more proper beam hardening correction. This is also led to deciding higher-precision pixel values of an image, thus providing the image with more improved quantitative performance and reducing unevenness among the pixels due to irregularities caused inherently to the pixels.

BRIEF DESCRIPTION OF DRAWINGS

In the accompanying drawings:

FIG. 4 is a flowchart explaining a postprocess including a data acquisition process and another part of the image processes, which are performed in the X-ray apparatus;

FIG. 12 shows tables exemplifying the fitting coefficients stored as part of the beam hardening correcting information;

FIG. 16 is a graph explaining how to correction the beam hardening by using a generalized beam hardening correction curve and the target function (a linear line of X=Y) regarding a single atomic number;

FIG. 17 shows tables pictorially exemplifying, every pixel and as every energy bin, beam hardening correcting information and effective atomic numbers $Z_{\mathit{eff}}$, which are stored in a memory;

FIG. 21 is a table partly and pictorially explaining contents stored in an image memory for displaying images;

DESCRIPTION OF EMBODIMENTS

Hereinafter, embodiments according to the present invention, which are directed to a method and an apparatus for processing measurement data in photon counting X-ray detection and a photon counting X-ray apparatus, will now be described with reference to the accompanying drawings.

First Embodiment

With reference to FIGS. 1 to 19, a method and an apparatus, which is according to the present invention, for processing measurement data in photon counting X-ray detection (hereinafter, referred to as a data processing method and a data processing apparatus) will now described. These data processing method and apparatus are installed or mounted in, for example, X-ray mammography apparatuses, medical X-ray apparatuses such as dental X-ray imaging apparatuses, or X-ray apparatuses such as foreign matter inspection apparatuses.

Figure 1:
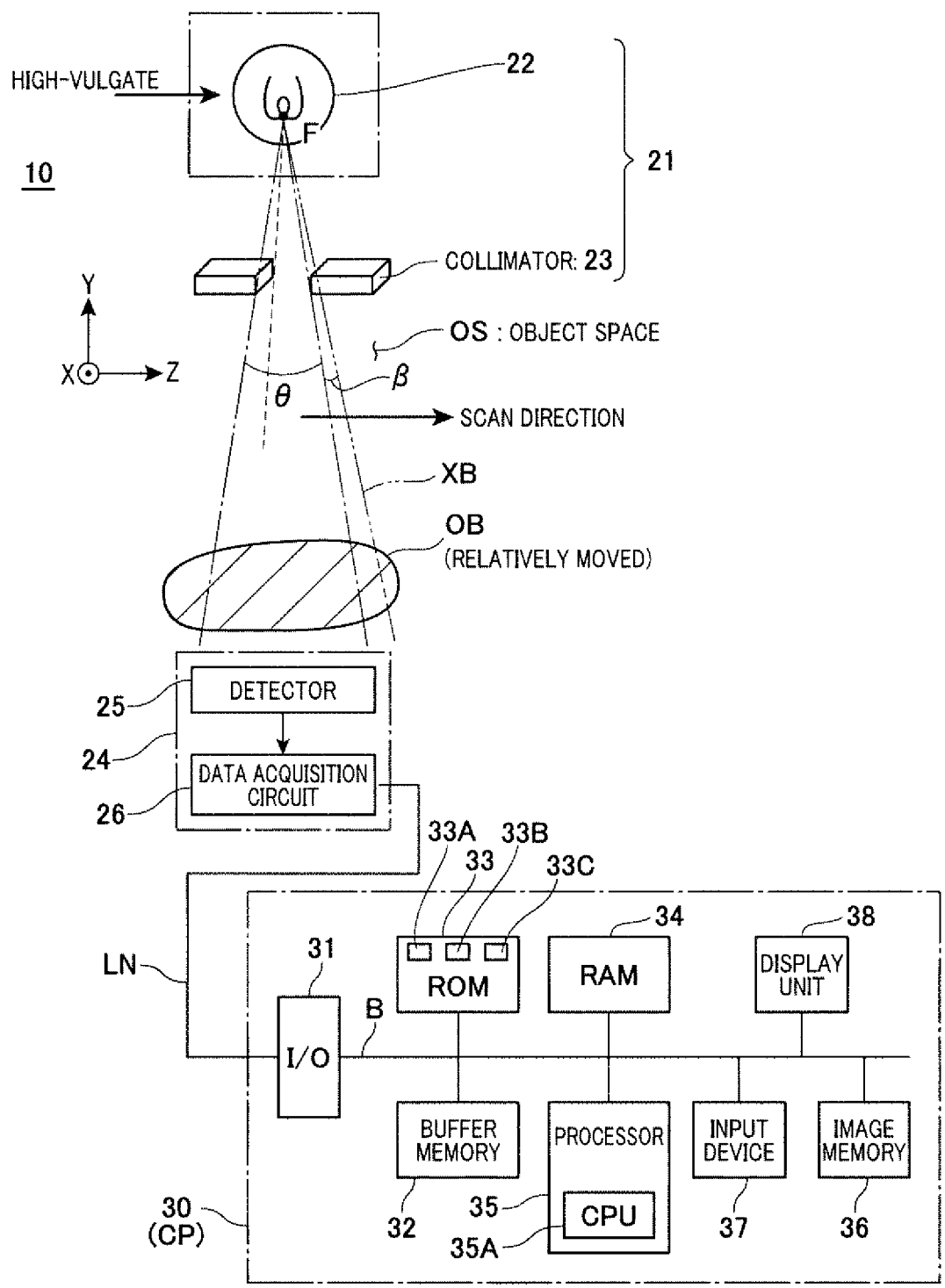
FIG. 1 is a block diagram outlining the configuration of an X-ray apparatus according to one example of an X-ray apparatus in which an image processing apparatus (performing an image processing method) according to the present invention is mounted.

FIG. 1 exemplifies a main configuration of an X-ray apparatus 10. The hardware configuration itself of this X-ray apparatus is known although the data processing method and apparatus according to the first embodiment is installed or mounted in this X-ray apparatus, so that the hardware configuration is explained for its key components.

As shown in FIG. 1, the X-ray apparatus 10 is provided with an X-ray generator 21 which generates X-rays with a continuous X-ray spectrum and collimates the X-rays into beam-formed X-rays, and radiates the beam-formed X-rays to an object space OS. The X-ray generator 21 is provided with an X-ray tube 22 driven by a high voltage supplied and a collimator 23 arranged in front of the X-ray tube 22 to collimate the X-rays generated by the X-ray tube 22 into a beam form. The X-ray tube 22 has a tube focal point F whose focal radius is 0.5 mmϕ, for instance. Hence, the tube focal point F can be regarded as a substantial spot-shaped X-ray source. The X-rays emitted from this tube focal point F is ray fluxes of photons which have various energy amounts (X-ray energy amounts) such that the X-rays have a continuous energy spectrum depending on a tube voltage applied to the X-ray tube.

The X-ray apparatus 10 is also provided with a detector 24 which detects the beam-formed X-rays which have been radiated and transmitted through an object OB being imaged which is located in the object space OS. The detector 24 includes a receiving window and a detection layer 25 arranged immediately below the receiving window. The detection layer 25 has a layer made of semiconductor material (such as CdTe or CZT) which directly converts the X-rays to electric signals. In this detection layer 25, pixels each having for example a pixel size of 200 µm×200 µm are arranged two-dimensionally as a group of pixels.

The detector 24 is also provided with a layered data acquisition circuit 26 which is built, for example, as an ASIC layer and intended to process each pixel defection signal pixel by pixel. The data acquisition 10o circuit 26 is placed on a side of the detection layer 25, which is to the tube focal point F. The data acquisition circuit 26 is provided as a photon counting circuit capable of counting, every pixel, the number of X-ray photons received by the pixels of the detection layer 25. In addition, this circuit enables thresholds for discriminating X-ray energy amounts to be set, such that the X-ray spectrum is divided into a plurality of X-ray energy ranges (also referred to as bins). Hence, the number of photons can be counted every pixel in each of the energy bins.

As a result, from the layered data acquisition circuit 26, count data made by processing electric pulse signals acquired in response to an incident event of each X-ray photon are outputted as frame data (a set of count data at each pixel. A frame rate varies from, for example, 300 to 6,600 fps, at which of which the single frame data are outputted. Except for occurrence of a pileup phenomenon of incident photons entering a single pixel, every time a single photon enters at one pixel, a one electric pulse will be excited, thereby the count data at each pixel reflecting the number of electric pulses at each pixel.

Figure 2:
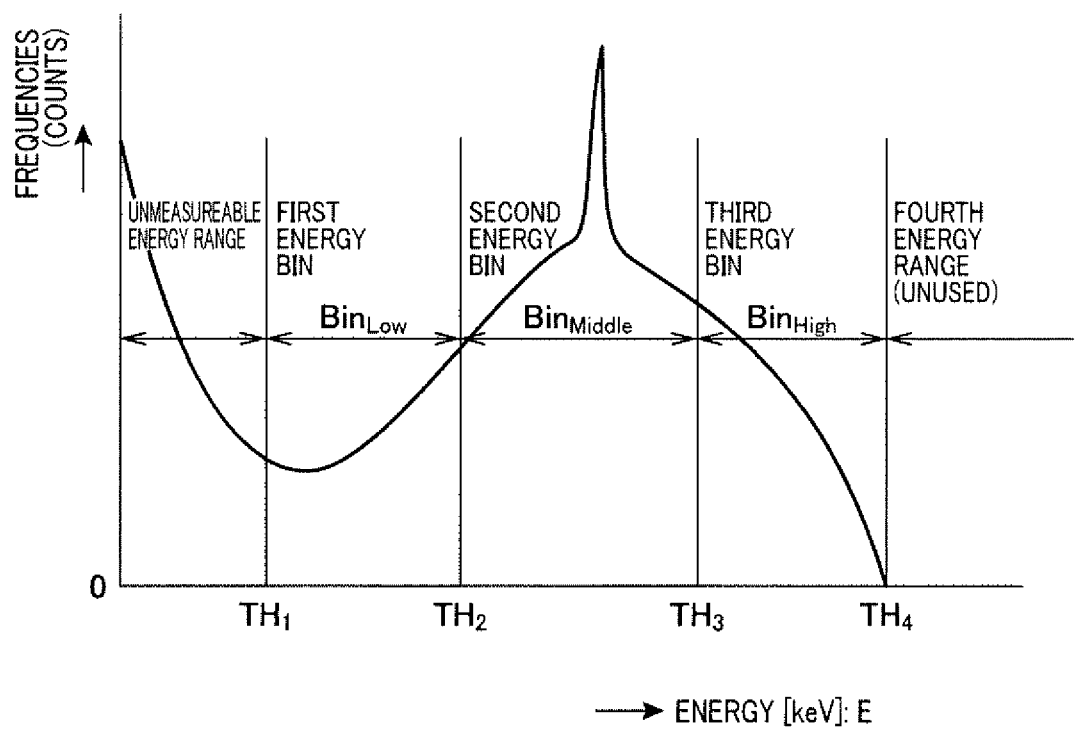
FIG. 2 is a graph exemplifying a continuous spectrum of polychromatic X-rays and three X-ray energy bins.

As stated, the detector 24 is categorized into a photon counting detector (a photon counting type of detector) in terms of how to detect X-rays. Practically, the detector 24 regards, as an aggregation of photons having various amounts of energy, the X-rays (polychromatic X-rays) having a continuous energy spectrum, and has a configuration which counts the number of photons every X-ray energy bin (range) and every pixel (incidentally, the pixels may be one, or two or more in number). As shown in FIG. 2, the X-ray energy bins are set for example as three energy bins $Bin_{Low}$ to $Bin_{High}$. The number of energy bins may be three or more, such as four or five, in number. In the energy spectrum [keV], an energy range lower than a lower-limit threshold TH1 and an energy range higher than an upper-limit threshold TH4 (which is set at the tube voltage in the example of FIG. 2) are set as being an unmeasurable range and an unused range, respectively. A range between the thresholds TH1 to TH4 is divided into a single range (in such a case, the thresholds are composed of only TH1 and TH4) or into a plurality of energy bins. For example, when thresholds TH2 and TH3 are set as shown in FIG. 2, there can be provided three energy bins.

The foregoing X-ray radiation/detection configuration is proposed by WO 2015/111728 A1 or other patent publications.

An object OB positioned in the object space OS is scanned by the beam-formed X-rays. For this purpose, a pair of the X-ray generator 21 and the detector 24 is relatively moved to the object OB, or vise verse. One example is an X-ray foreign matter inspection of food or other items, in which a belt conveyer is arranged to pass through the object space OS. An object OB on this belt conveyer is thus X-ray scanned. One of medical systems is a dental panoramic X-ray imaging apparatus, in which the object space OS is formed between the X-ray generator 21 and the detector 24 and an object OB, that is, a patient's jaw, is positioned in the object space OS. In this imaging posture, the pair of the X-ray generator 21 and the detector 24 is rotated around the patient's jaw for X-ray scanning. This configuration is also true of an X-ray mammography apparatus which is one type of medical system. In short, it is sufficient to provide a relative movement between the pair of the X-ray generator 21 and the detector 24 in scanning the object OB.

The count data outputted from the detector 24 as digital amounts are then subjected to a process which utilizes merits of the energy discrimination method. This process is carried out by a processor mounted in the X-ray apparatus 10 or a processor arranged outside the X-ray apparatus 10. This process includes reconstructing images based on a tomosynthesis method, producing an absorption vector length image (a two-dimensional image) on the basis of the reconstructed image, and producing a three-dimensional scatter diagram on the basis of the reconstructed image. Processing for these images is proposed by WO 2016/171186 A1 or other patent publications.

In addition, in the present embodiment, the digital count data outputted from the detector 24 is also subjected to a process which is inherent to the present invention. This process includes beam hardening correction which makes it possible that corrected results of the count data provisionally estimated using an assumed beam hardening correction curve come closer to their true values retrospectively. This process is still effective for substances of a wide range of effective atomic numbers $Z_{eff}$, with a smaller amount of calculation. In the present embodiment, the beam hardening correction curve is adopted as a curve used to adjust a beam-hardened attenuation characteristic of a substance to a target function (i.e., a linear attenuation characteristic compared to a weight thickness of the substance to which monochromatic X-rays are radiated). Depending on a difference between the beam hardening correction curve and the target function, the count data (count values or counts) are corrected.

As stated, the beam hardening is a phenomenon occurring when radiated polychromatic X-rays pass through a substance, due to the fact that lower X-ray energy components are likely to be absorbed or scattered in the substance more than those for higher X-ray energy components. This phenomenon appear such that, after transmission of the X-rays through a substance, X-ray components in a higher energy range becomes larger in their ratios than those in a lower energy range, resulting in that an effective (average) energy amount is shifted to its higher energy side. For this reason, from a physical point of view, the beam hardening phenomenon can be summarized such that this phenomenon is caused from differences in mutual interactions between molecules (atoms) and X-ray photons of an object, in which such differences are originated from different X-ray photon energy amounts. Further, the effective atomic number $Z_{eff}$ is an average atomic number of atomic numbers of a plurality of types of elements (substances) which are present in a beam-formed X-ray transmission path in an object, in which mutual interaction amounts to the X-rays being reflected in the average atomic number.

The X-ray apparatus 10 according to the present embodiment is provided with a data processing apparatus 30, which is, as shown in FIG. 1, provided as a computer CP. This computer CP itself can be provided as a computer with known calculation functions, and is provided with an interface (I/O) communicably connected to the detector 24 via a communication line LN. In the interface 31, a buffer memory 32, a ROM (read-only memory) 33, a RAM (random access memory) 34, a processor 35 equipped with a CPU (central processing unit) 35A, an image memory 36, an input device 37, and a display unit 38, which are mutually communicably connected via an internal bus B.

The ROM 33 is provided to previously store therein computer-readable programs for correcting counts and identifying substances (materials), which enable the data processor 35 to read the programs and store them in its work area for execution of the programs. For this purpose, the ROM 33 is provided with a program storage area (functioning as a non-transitory computer recording medium) for previous storage of such programs. The ROM 33 is also provided with first and second storage areas 33B and 33C which stores therein beam hardening correcting data (which are also referred to as calibration data) for beam-hardening correcting the measures counts, which will so be detailed later.

The processor 35 (that is, the CPU 35A) reads necessary programs from the program storage area 33A of the ROM 33 into its own work area. The processor 35 includes a CPU dedicated to image processing. The buffer memory 32 is provided to temporarily memorize the frame data sent from the detector 24. The RAM 34 is provided to temporarily memorize data required during processing of the processor 35.

The image memory 36 is provided to store therein various image data and various kinds of information processed by the processor 35. The input device 37 and the display unit 38 function as a man-machine interface with users, in which the input device 37 receives input information given by users and the display unit 38 presents images and other information under control of the data processor 35.

The data processing apparatus 30 can be installed as an apparatus integrated with the X-ray device 10 or an inspection system. As in the present embodiment, the data processing apparatus 30 can be communicably connected to the X-ray apparatus 10 via the communication line LN. In this configuration, the line may be always-on connection or on-demand connection. In addition, the data processing apparatus 12 can be provided as a stand-alone type apparatus. Alternatively, the data processing apparatus 30 may be configured by a hardware circuit which performs pipeline processing.

<Data Processing Apparatus and Data Processing Method>

The data processing method according to the present invention will now be described. This data processing method is carried out by the processor 35 (i.e., the CPU 35A) in the data processing apparatus 30. The processor 35 reads a predetermined program for the data processing from the storage area 33A and performs steps of the program.

<Part 1: Preprocess>

Preprocessing for the beam hardening correction, which is a part of the data processing method, will now be described.

Compared with the conventional beam hardening correction, the beam hardening correction according to the present invention is more advantageous in that i) it is possible to, using correcting data prepared by a one-time previous preparation, cope with a wider range (Zmin to Zmax) of the effective atomic numbers $Z_{eff}$ presented by a plurality of substances (materials) which are present in an X-ray radiation path, and ii) it is possible to perform the beam hardening correction at a higher level of accuracy.

Figure 3:
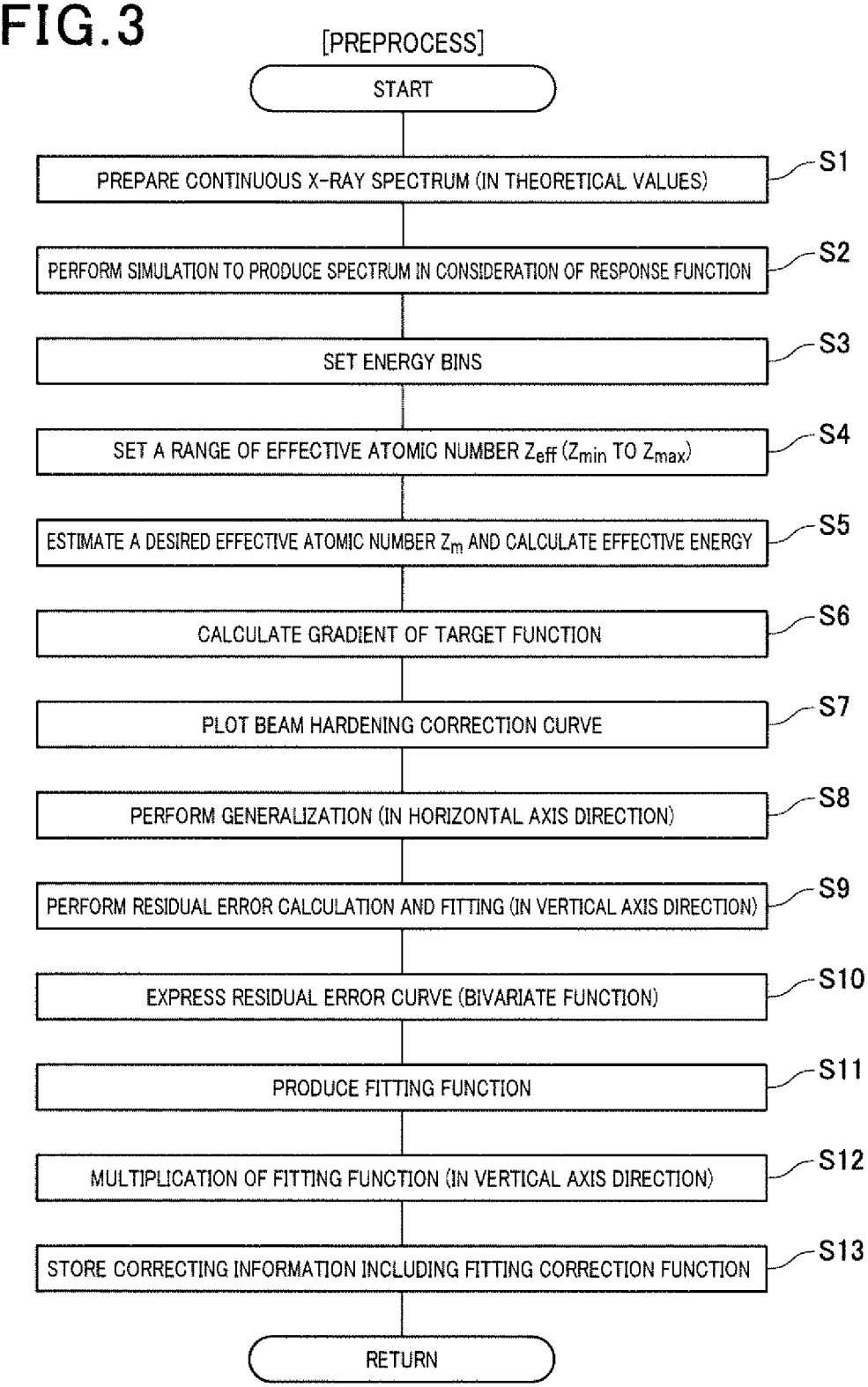
FIG. 3 is a flowchart explaining a preprocess carried out as a part of image processes in the X-ray apparatus according to the embodiment.
Figure 5:
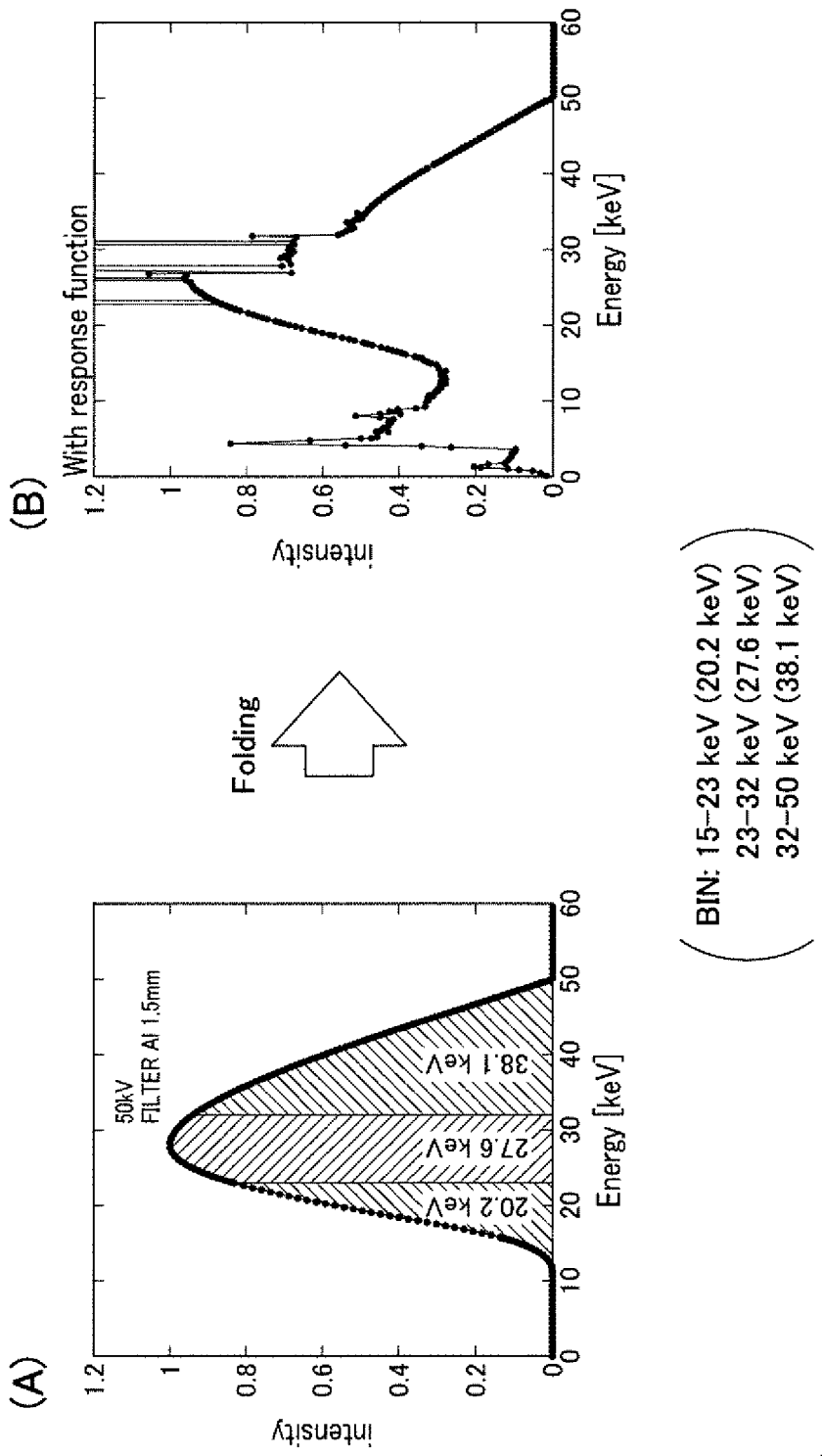
FIG. 5 shows graphs exemplifying a continuous spectrum of polychromatic X-rays simulated in consideration of response functions of a detector and used for estimating an effective atomic number $Z_{eff}$.
Figure 6:
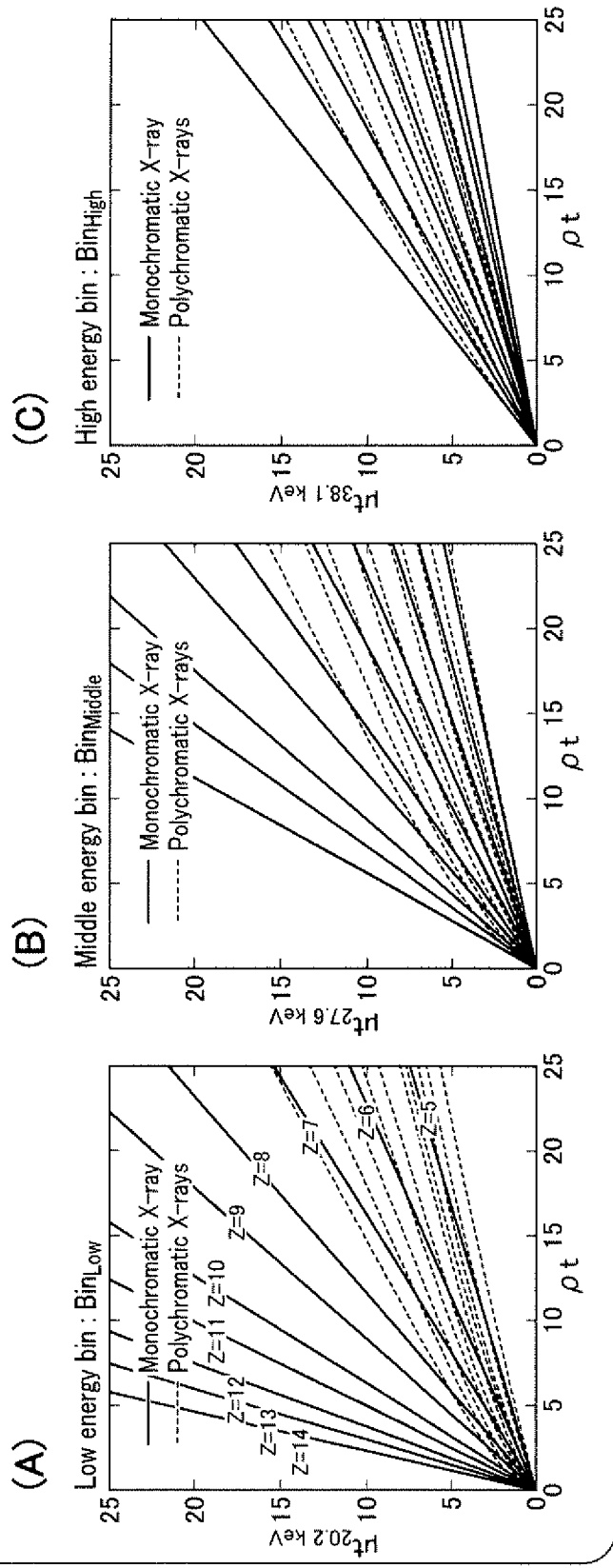
FIG. 6 shows graphs exemplifying both i) theoretical attenuation characteristics (plotted as solid lines; linear characteristics in graphs (A) to (C) of FIG. 6) obtained when monochromatic X-rays are radiated to substances whose atomic number Z=5 to 14 in each of three X-ray energy bins which were set to the X-ray energy spectrum and ii) theoretical attenuation characteristics (plotted as dotted lines; curved characteristics in graphs (A) to (C) of FIG. 6) obtained when polychromatic X-rays are radiated to the foregoing substances in the same manner as that used In radiating the monochromatic X-rays.

As such a previous preparation, the preprocessing can be performed interactively with an operator by the processor 35 according to the steps shown in FIG. 3.

First of all, theoretical values of a continues X-ray (polychromatic X-ray) energy spectrum to be radiated by the X-ray tu e 22 are prepared (step S1 in FIG. 3). This theorical spectrum is shown in a part (A) of FIG. 1. The theorical spectrum is then applied to Monte Carlo simulation to make an energy spectrum in which response functions based on semiconductor materials of the detector 12, thicknesses of the materials, a pixel size, and other factors are folded (step S2). A part (B) of FIG. 5 exemplifies an energy spectrum in which the theoretical speculum is submitted to folding with the response functions. To this energy spectrum, three energy bins (ranges) are set (step S3), which are, from a lower energy side, a lower energy bin: $Bin_{Low}$ (15 to 23 keV (20.2 ke)), a middle energy bin: $Bin_{Middle}$ (23 to 32 keV (27.6 keV)), and a higher energy bin: $Bin_{High}$ (32 to 50 keV (38.1 keV)). The numeral values in the brackets, 20.2 keV, 27.6 keV, 38.1 keV, are effective energy amounts in the respective energy bins. This effective energy amount has a mass attenuation coefficient $\mu/\rho$ (wherein $\mu$ is a linear attenuation coefficient and $\rho$ is a mass density) corresponding to the gradient of a target function in each of the energy bins.

Then, as to tissues (substances) of an object being inspected, a range of Zmin to Zmax of the effective atomic number $Z_{eff}$ (for example, Zmin=5 and Zmax=14, which are positive integers) is set interactively (step S4). This range is decided to cover effective atomic numbers which are assumed to appear in the actual clinical setting. In addition, from this range Zmin to Zmax of the effective atomic number $Z_{eff}$, a desired effective atomic number Zm (for example Zm=7) is decided as a reference interactively with the operator (step S5).

An effective energy amount is then calculated for each of the three energy bins; $Bin_{Low}$ to $Bin_{High}$ (step S5). Moreover, the foregoing mass attenuation coefficient $\mu/\rho$ is calculated as a gradient of the target function (step S6). This mass attenuation coefficient $\mu/\rho$ is set as a value which is regarded as corresponding to the effective amount in each of the respective energy bins; $Bin_{Low}$ to $Bin_{High}$ and provisionally regarded as the reference effective atomic number Zm.

Then, to each of the energy bins; $Bin_{Low}$ to $Bin_{High}$, a beam hardening correction curve is plotted in a two-dimensional coordinate (step S7). Plotting this curve is performed using already physically known data (that is, theoretically know calculated values). Practically, as shown in parts (A), (B) and (C) of FIG. 6, the two-dimensional coordinate has a horizontal axis assigned to a mass thickness ($\rho t$) and a vertical axis assigned to an X-ray attenuation amount ($\mu t$) corresponding to an effective energy amount in each of the energy bins. In each of the respective energy bin graphs, solid lines indicate linear theoretical attenuation characteristics (corresponding to the foregoing target functions). These linear characteristics are obtained in a case where monochromatic X-rays showing a single linear peak in the X-ray spectrum are radiated to substances having atomic numbers Z=7, 8, 9, . . . , 13 and 14. In contrast, dotted lines indicate theoretical attenuation characteristics of the counts obtained in a case where polychromatic X-rays whose energy spectrum has a continuous distribution are radiated to the substances having atomic numbers Z=7, 8, 9, . . . , 13 and 14. When the polychromatic X-rays are radiated to substances, the beam hardening is caused in the substances, as stated. Hence, as the mass thickness ($\rho t$) increases, the rate of increase in the X-ray attenuation amount $\mu t$ decreases in the attenuation characteristics.

Further, for each of the energy bins; $Bin_{Low}$ to $Bin_{High}$, the values ($\rho t$) of the horizontal axis is multiplied by the gradient, i.e., the mass attenuation coefficient $\mu/\rho$, of the forgoing target function, so that the values of the horizontal axis is generalized (step S8). The mass attenuation coefficient $\mu/\rho$ is a known value which can be decided by using an atomic number Z and X-ray energy amounts.

Figure 7:
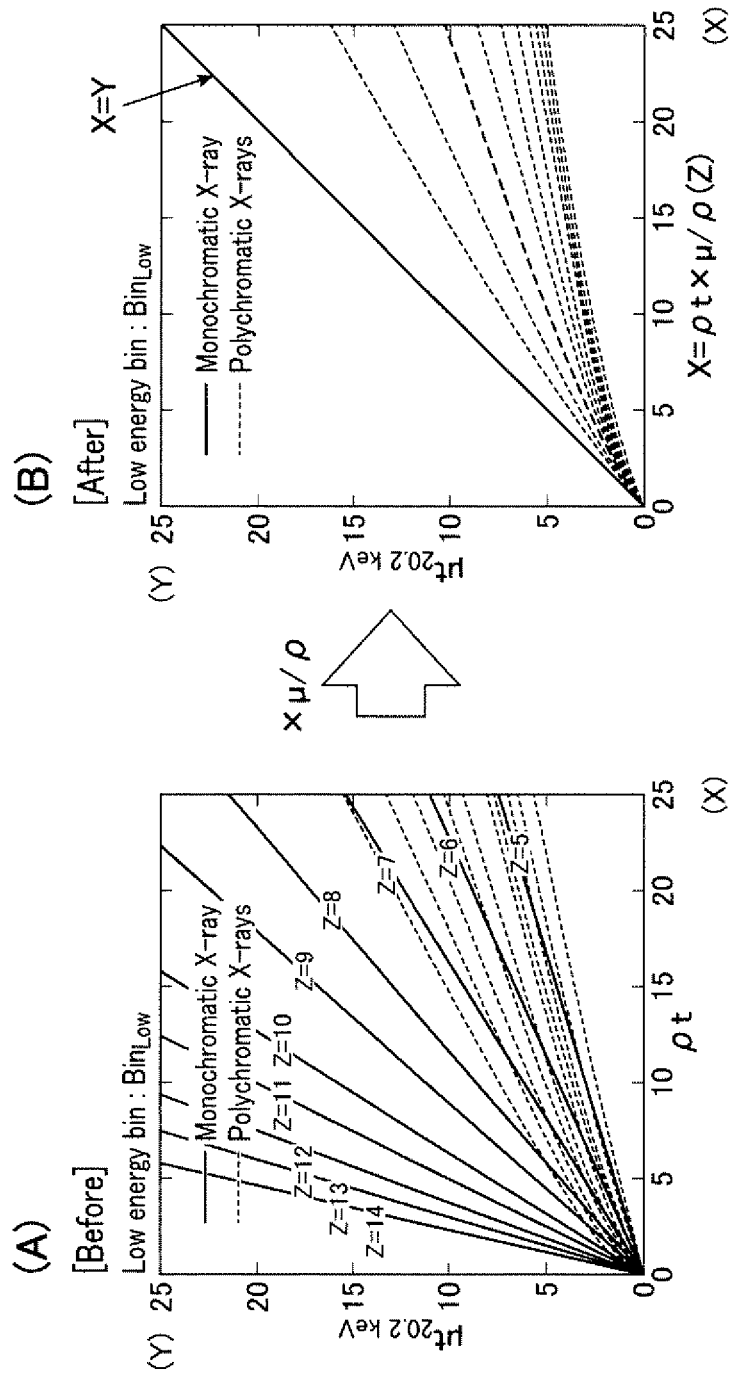
FIG. 7 shows graphs exemplified in a lower energy bin, the graphs explaining generalizing, in the horizontal axis direction, both the theoretical attenuation characteristics (in the graph (A) of FIG. 7; solid lines showing the linear characteristics) gained in the monochromatic X-ray radiation and the theoretical attenuation characteristics (in the graph (A) of FIG. 7; dotted lines showing the curved characteristics) gained in the polychromatic X-ray radiation, whereby both a target function (a solid line shown in the graph (B) of FIG. 7: a linear characteristic of X=Y) and a beam hardening correction curve (dotted lines shown in the graph (B) of FIG. 7; curved characteristics) are produced.

To be specific, FIG. 7 explains about the generalization for the lower energy bin: $Bin_{Low}$. By this generalizing calculation, a graph [Before] shown in a part (A) of FIG. 7 is transformed to a graph [After] shown in a part (B) of FIG. 7. In the graph [After], the horizontal axis indicates values defined by $X=\rho t\times\mu/\rho(Z)=\mu t$, resulting in that the horizontal axis shows the same dimension as $\mu$ of the vertical axis (Y-axis), (i.e., X=Y).

Different types of substances have different atomic numbers Z (which are led to different effective atomic numbers $Z_{eff}$), which result in different degrees of occurrence of the bean hardening phenomenon. Hence, the atomic numbers Z serve as a variable to the respective curves (linear lines).

As understood from the part (B) of FIG. 7 marked by [After], the generalizing calculation in the horizontal axis direction makes it possible that the target functions (that is, corresponding to attenuation characteristics with no beam hardening phenomenon caused thanks to radiation of monochromatic X-rays) to the respective atomic numbers Z=7, 8, 9, . . . , 13, 14 become the same and are equal to a function of X=Y. As a result, curves obtained when polychromatic X-rays are radiated to substances having the atomic numbers Z=7, 8, 9, . . . , 13, 14, that is, beam hardening correction curves for correcting attenuation characteristics which suffer from the beam hardening phenomenon, can be estimated by using information indicating a shift amount from the linear line of X=Y in the vertical axis direction (Y-axis). For this reason, in the present embodiment, in setting the beam hardening correction curve to the atomic numbers Z=7, 8, 9, . . . , 13, 14, the shifted amounts thereof can be set using, as a sole variable, the atomic number Z only. Accordingly, in the present embodiment, this setting process is referred to as generalization. Practically, amounts of such shifts from the linear line of X=Y can be stored (saved) for each of the atomic number Z (=7, 8, 9, . . . , 13, 14), so that, when an atomic number Z=8 is designated for instance, an amount of shift of the curve Z=8 from the linear line X=Y is read, and is used to easily calculate a target function The above generalization can also be applied to the middle energy bin; $Bin_{Middle}$ and the higher energy bin; $Bin_{High}$.

Figure 8:
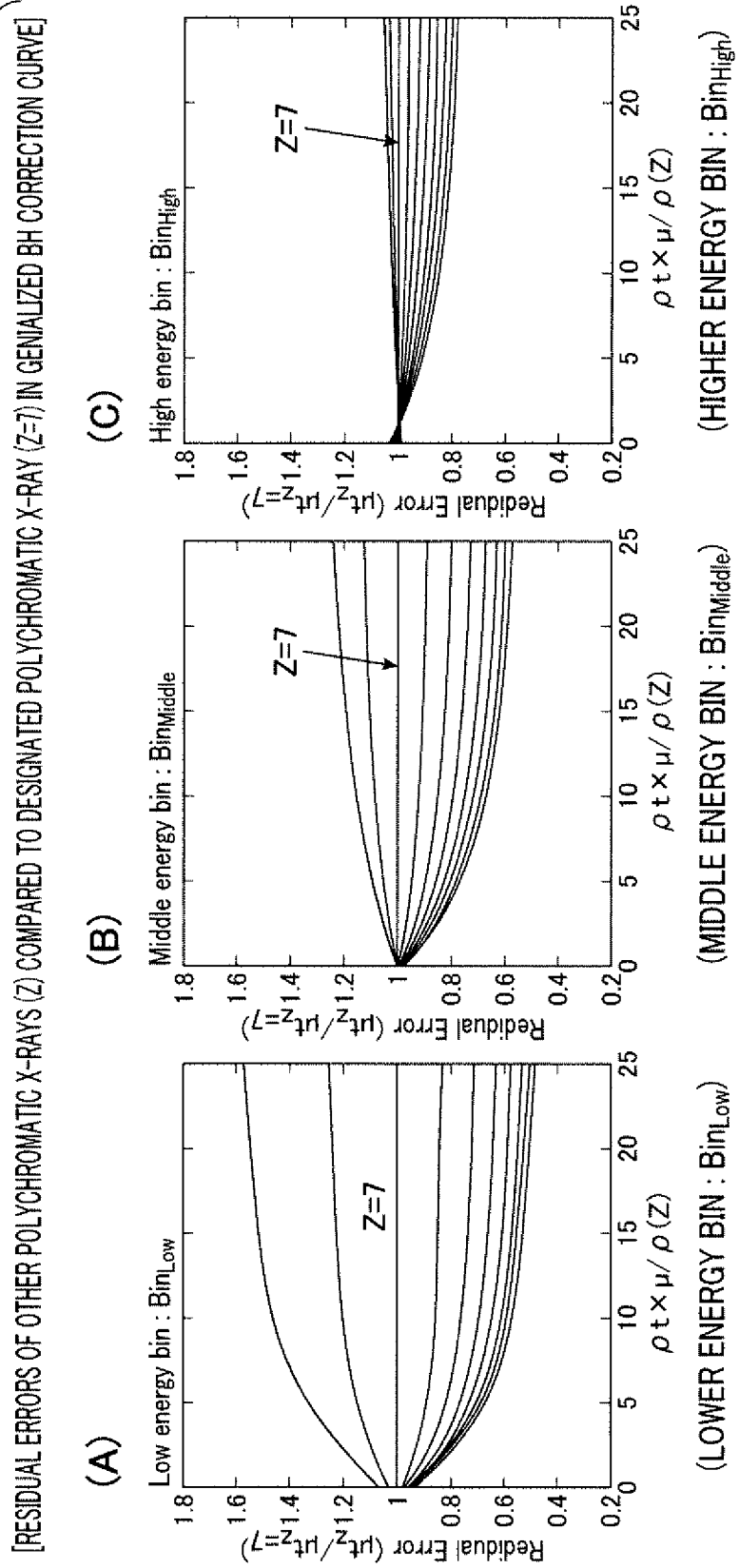
FIG. 8 shows graphs exemplifying residual errors in the vertical axis direction between a beam hardening correction curve designated to a specific atomic number Z and other beam hardening correction curves, among the generalized beam hardening correction curves related to the substances having the forgoing atomic numbers.
Figure 9:
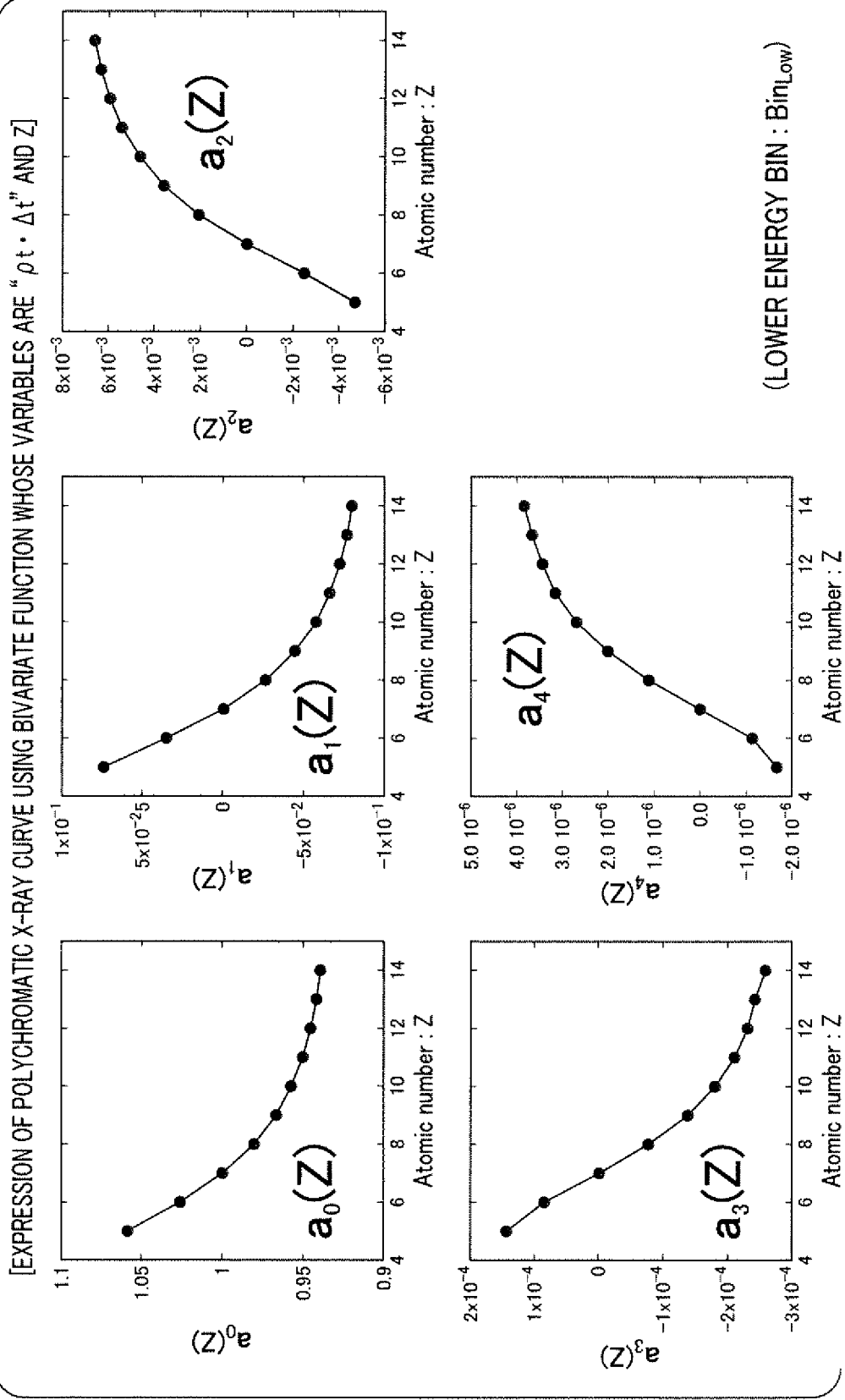
FIG. 9 shows graphs exemplifying, in the lower energy bin, fitting coefficients of fitting functions used for the foregoing residual errors in the vertical axis direction.
Figure 10:
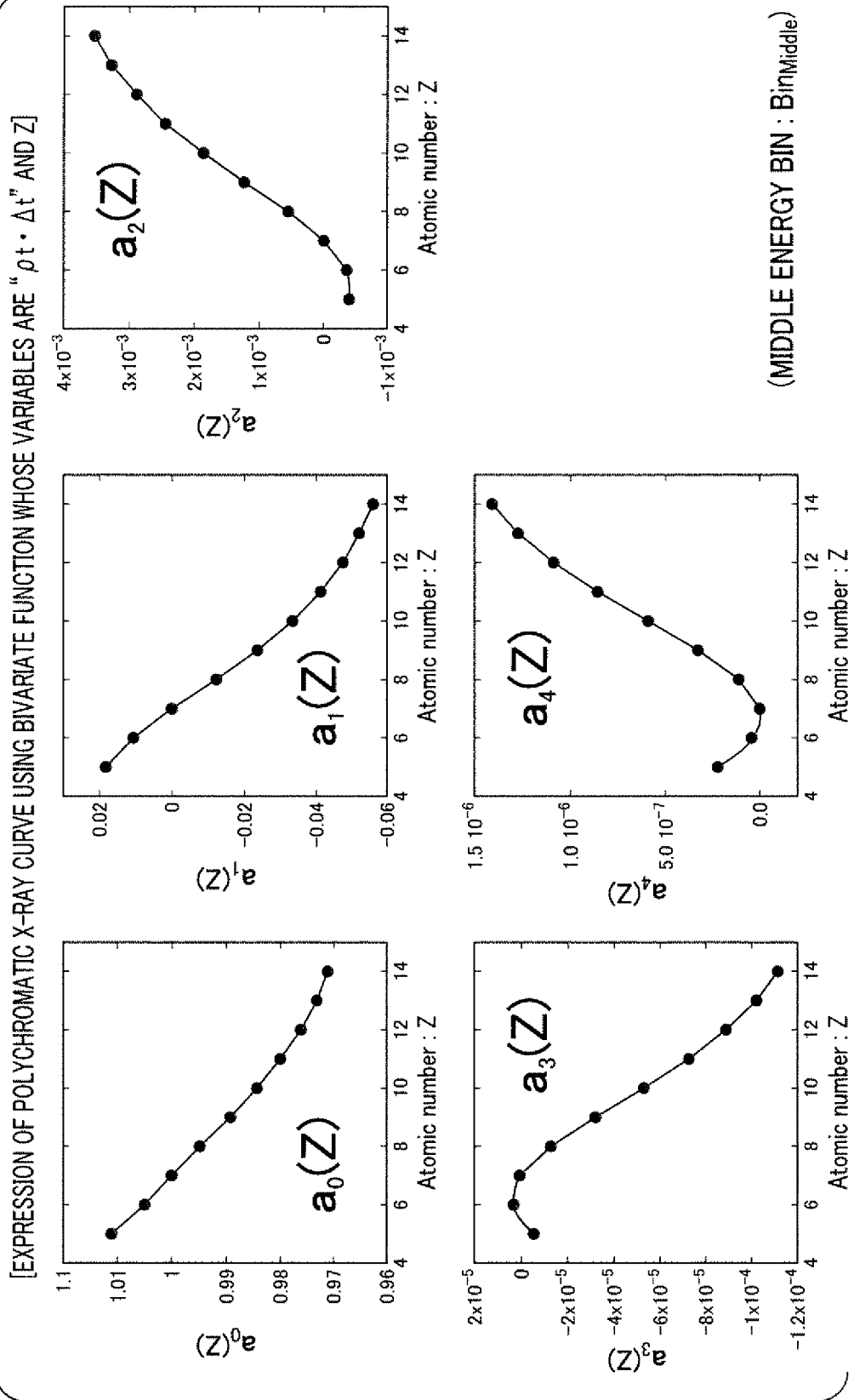
FIG. 10 shows graphs exemplifying, in a middle energy bin, fitting coefficients of fitting functions used for the foregoing residual errors in the vertical axis direction.
Figure 11:
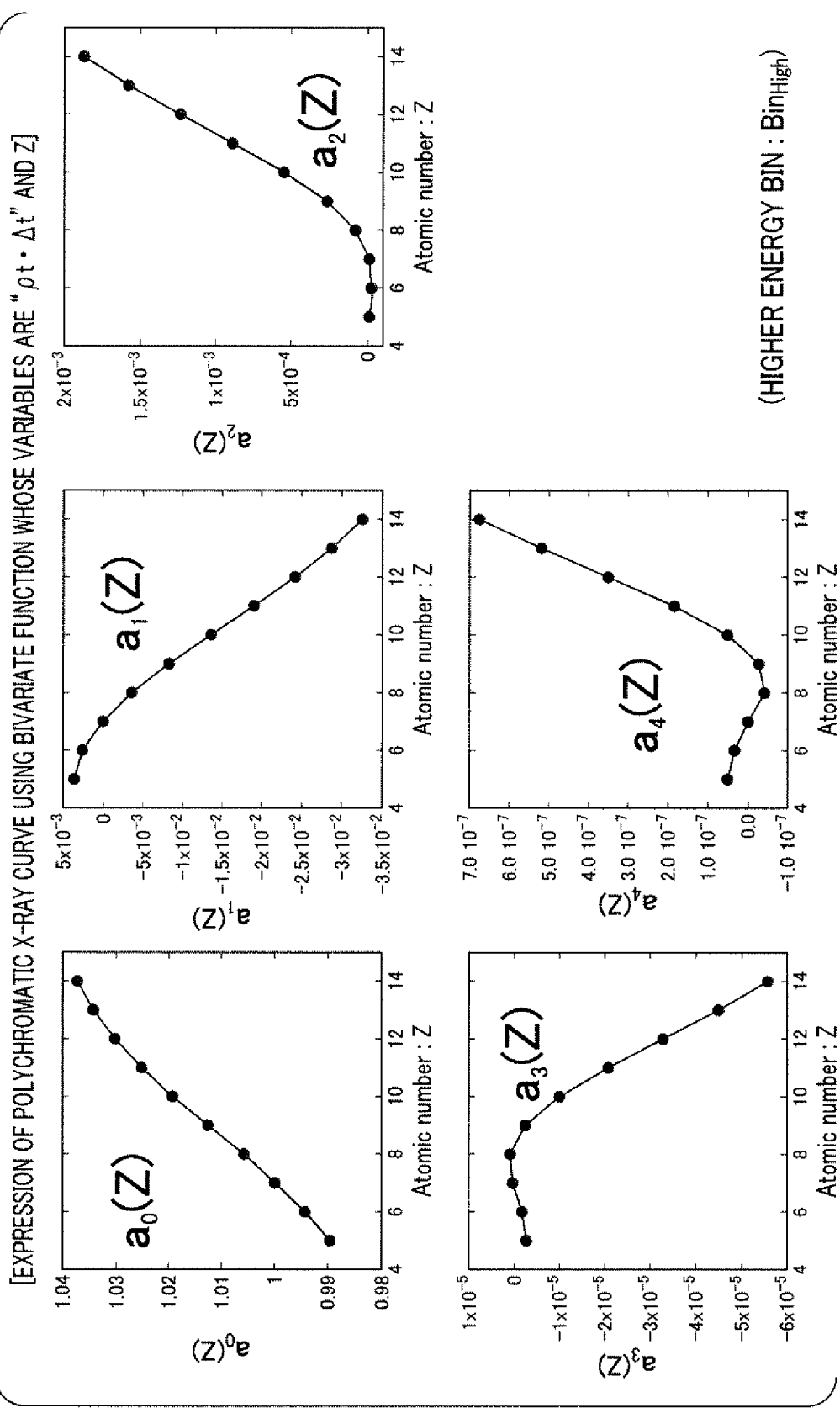
FIG. 11 shows graphs exemplifying, in a higher energy bin, fitting coefficients of fitting functions used for the foregoing residual errors in the vertical axis direction.

The processor 35 then proceeds to a process of calculating residual errors and fitting (step S9). This process is detailed as follows. Among the generalized beam hardening correction curves, a correction curve is employed as a reference. This employed correction curve is for example a correction curve directed to polychromatic X-rays to be radiated to a substance of an atomic number Z=Zm (a designated Z=7). Residual errors are then calculated between this reference curve and each of curves directed to the other atomic numbers Z (=5, 6, 8, 9, . . . , 13, 14), and the calculated residual errors are fit with use of a biquadratic function, every energy range. Graphs (A), (B) and (C) of FIG. 8 show residual error (ratio) curves calculated for each of the energy bins: $Bin_{Low}$, $Bin_{Middle}$, $Bin_{High}$. In the graphs, the vertical axis is assigned to a residual error of "$\mu t_Z/\mu t_{Z=7}$" corresponding to a residual error ratio. A linear line at $\mu t_Z/\mu t_{Z=7}=1$ expresses a residual error ratio when Z=7, in which this ratio is 1 and constant. The residual errors in lower energy bins are larger than those in higher energy bins. The reason is that influence of the beam hardening on the X-ray photons becomes stronger as the X-ray photon energy becomes lower.

In the foregoing example, the biquadratic function is used as the fitting function, but it is not always necessary to use the biquadratic function. By use of functions having higher dimensions, the residual errors can be fitted with higher accuracy. As to use of a function having which degree of dimension can be decided in consideration of calculation amounts.

Then, the processor 35 expresses residual error curves as bivariate functions having as two variables "mass thickness $(\rho t)\times\Delta$" and an atomic number Z (step S10). The foregoing fitting coefficients of a biquadratic function is expressed as a function of the atomic number Z such that beam hardening correction curves can be estimated for any atomic number Z selected from a desired range of atomic numbers Zmin to Zmax. The bivariate functions for each of the energy bins are exemplified in FIGS. 9 to 11

Based on the above steps, a fitting function $f(\rho t)$ comprehensively expressing the foregoing bivariate functions (i.e., expressing the residual errors) can be made as a following formula (step S11).

$$f(\rho t)=a_0+a_1\times(\rho t)+a_2\times(\rho t)^2+a_3\times(\rho t)^3+a_4\times(\rho t)^4 \quad (1)$$

In this formula, Z denotes an effective atomic number and $M_j(j=0\sim4)$ denote coefficients, and $a_j(J=0\sim4)$ denote coefficients that are expressed by the following formulae.

$$a_0=M_0+M_1\times Z+M_2\times Z^2+M_3\times Z^3+M_4\times Z^4$$

$$a_1=M_0+M_1\times Z+M_2\times Z^2+M_3\times Z^3+M_4\times Z^4$$

$$a_2=M_0+M_1\times Z+M_2\times Z^2+M_3\times Z^3+M_4\times Z^4$$

$$a_3=M_0+M_1\times Z+M_2\times Z^2+M_3\times Z^3+M_4\times Z^4$$

$$a_4=M_0+M_1\times Z+M_2\times Z^2+M_3\times Z^3+M_4\times Z^4 \quad (2)$$

Aa understood, the coefficients $a_j(j=0\sim4)$ are functions of the atomic number Z and the coefficients $M_j(j=0\sim4)$ are amounts which are dependent on the coefficients $a_j$. These fitting coefficients $M_j$ and $a_j$ are pictorially exemplified in tables (A), (B) and (C) of FIG. 12, every energy bin.

As a result, the final beam hardening correction functions serving as correcting information are obtained, in each of the energy bins, by multiplying an estimated attenuation characteristic curve of a substance having an atomic number Z=Zm=7 specified in estimated attenuation characteristics generalize every energy bin, by the forgoing function $f(\rho t)$ (step S12). Hence, as exemplified in graphs (A), (B) and (C) of FIG. 13, the beam hardening correction functions, which can be used as final beam hardening correction information, can be provided in the predetermined range of atomic numbers, every energy bin The processor 35 saves the above beam hardening correction functions into, for example, the first storage area 33B (or the second storage area 33C) as the beam hardening correcting information (step S13). In response to designating an atomic number Z, the processor 35 reads a beam hardening correction function corresponding to the designated atomic number Z is thus read into its work area. The read correction function is used to perform the beam hardening correction in the same manner as conventional methods. An example of such correction will be detailed later.

As a modification for saving the correcting information, information about the estimated attenuation characteristic curve of the substance having the atomic number Z=Zm=7 designated among the generalized estimated attention characteristics and fitting coefficients $M_j$ and $a_j$ of the foregoing fitting function $f(\rho t)$ for each energy bin may be saved previously in the first storage area 33B (or the second storage area 33C) of the ROM 33, for example. In such a modification, the saved information is read when being necessary and a beam hardening correction function for a desired atomic number Z is calculated for performing the beam hardening correction.

<Part 2: Acquisition Process and Postprocess (Including Beam Hardening Correction and Producing Effective Atomic Number Image)>

When the forgoing preprocess is completed, the processor 35 is ready for an interaction with an operator as shown in FIG. 4, in which acquisition of X-ray transmission data and a subsequent postprocess can be performed.

The processor 35 operates to cause relative movement between a pair of the X-ray generator 21 and the detector 24 and an object OB, during which a not-shown high voltage generator is controlled to drive the X-ray tube 22 and, concurrently, the detector 24 is driven, whereby beam-formed X-rays scan the object OB. For example, in an X-ray foreign matter inspection, the pair of the X-ray generator 21 and the detector 24 is positionally fixed, while the object OB is moved to pass through the object space OS. In dental panoramic imaging, the pair of the X-ray generator 21 and the detector 24 is driven to rotate around a parietin's jaw which is the object OB, during which the X-ray generator 21 and the detector 24 are opposed to each other. Accordingly, the foregoing various modes of movement realize an X-ray scan, so that counts based on the number of photons of the X-rays which have been transmitted, with being attenuated, through the object are acquired as digital frame data in each of the three energy bins; $Bin_{Low}$, $Bin_{Middle}$, and $Bin_{High}$ (FIG. 4, step S21).

After this this data acquisition or concurrently with the data acquisition, the acquired frame data are subjected for example to a process based on a tomosynthesis technique, thereby producing an optimally (best) focused image in a view seeing the object OB along the X-ray radiation paths (step S22). This optically focused image may be an image along a section formed at a specified height (depth) in the object OB or an image collecting pixels which show an optimum (best) focus at each of the X-ray radiation paths passing the pixels respectively. Of course, the image may be a known vector length image proposed by the present inventors. Alternatively, the image can be provided as a simple transmission image on a scanogram technique. The data which are used for producing such images can be acquired in any one, or two or more selected from the three energy bins; $Bin_{Low}$, $Bin_{Middle}$, and $Bin_{High}$, or an energy bin produced by averaging such three energy bins.

The processor 35 then represents, on the display unit 38, the image produced at step S22 (step S23), and sets a ROI (region of interest) on that image interactively or automatically (step S24). One example such images and ROIs is pictorially shown in FIG. 14. In this example, an image IMOB of the object OB is presented on the display unit 38, on which an ROI designated by the operator is shown. The ROI indicates an area to which the beam hardening correction, later s described, is applied and an effective atomic number image thereof is produced. This designation of the area is not always necessary, and an alternative is to set, as the objective area, the whole displayed image of the object OB by default setting. Still alternatively, the ROI can be a plurality of ROIs which are used for designating the objective areas.

The processor 35 then proceeds to a step (step S25) in which, based on the frame data collected from the object OB placed in the object space OS, the number of truly emitted X-ray photons is used to calculate $\mu t$ (attenuation amount), every energy bin. This calculation is performed by using frame data collected through only the air, where an object is not placed in the object space OS. Such frame data are used prepared in advance as calibration data for the air.

Figure 15:
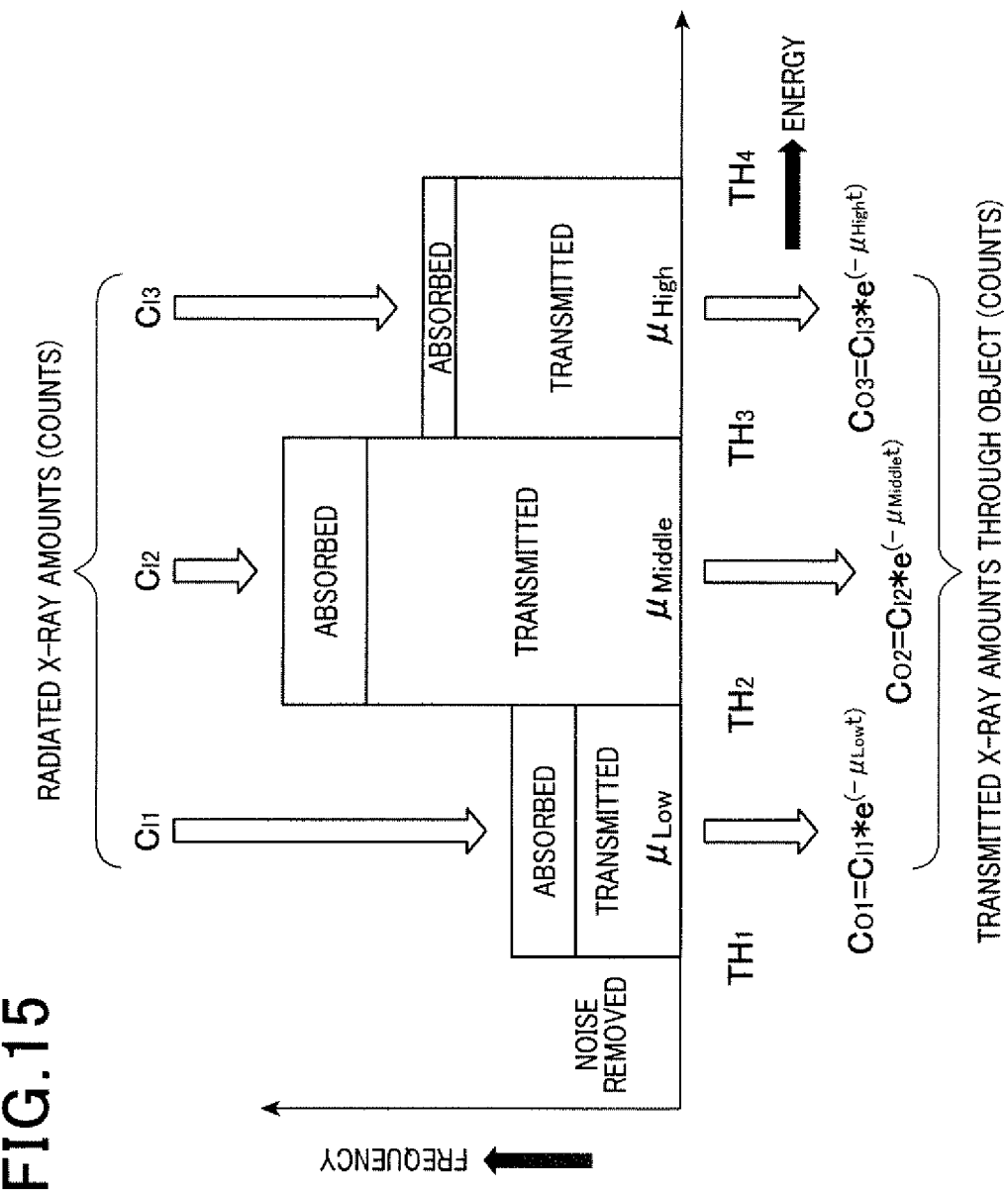
FIG. 15 is a graph showing, in each of the energy bins, a ratio between an incident X-ray photon count and an outputted X-ray photon count (i.e., a ratio between absorption and transmission of X-rays)

This will now be explained using FIG. 15. As shown, the X-ray energy bins: $Bin_{Low}$ to $Bin_{High}$ shown in FIG. 12 are pictorially shown along the horizontal axis in FIG. 15 and X-ray photon counts measured in each of the energy bins: $Bin_{Low}$ to $Bin_{High}$ are shown In the vertical axis. When radiating the X-rays whose energy spectrum is continuous, the X-ray photons are subjected to absorption and transmission thereof in and through the object, every energy bin, so that only X-ray photons which have been transmitted therethrough are detected. If denoting the number of incident photons in the respective energy bins: $Bin_{Low}$, $Bin_{Middle}$, and $Bin_{High}$ as $C_{ILow}$, $C_{IMiddle}$, and $C_{IHigh}$, the number of emitted photons, $C_{oHigh}$, $C_{oMiddle}$, and $C_{oHigh}$ can be expressed as follows:

$$Co_{Low} = C_{ILow} \cdot e^{(-\mu_{Low} t)}$$

$$Co_{Middle} = C_{IMiddle} \cdot e^{(-\mu_{Middle} t)}$$

$$Co_{High} = C_{IHigh} \cdot e^{(-\mu_{High} t)} \quad (3)$$

In these formulae, $\mu_{Low}$, $\mu_{Middle}$, and $\mu_{High}$ indicate estimated average linear attenuation coefficients in the respective energy bins: $Bin_{Low}$, $Bin_{Middle}$, and $Bin_{High}$ (practically, expressing linear attenuation coefficients respectively corresponding to effective energy amounts in the perspective energy bins), and t indicates a length (thickness) of the object in a transmission direction of X-ray fluxes. Further, it is premised that such estimated average linear attenuation coefficients $\mu_{Low}$, $\mu_{Middle}$, and $\mu_{High}$ are independent of the thickness t. Moreover, the number of incident photons: $C_{ILow}$, $C_{IMiddle}$, and $C_{IHigh}$ express data acquired with not object placed. Hence, at step S25, the foregoing formulae (3) are used to additionally calculate X-ray attenuation amounts $\mu_{Low} t$, $\mu_{Middle} t$, and $\mu_{High} t$ for each of the energy bins, every pixel or pixel area.

For performing the beam hardening correction, the processor 35 designate, as an initial value, an effective atomic number $Z_{eff}$ of one or more types of elements which are assumed to be included in the object OB or to compose the object OB. For example, $Z_{eff} = 7$ is designated (step S26). More practically, the object OB from which the data are acquired is a human breast for example, and the ROI is set at a portion which shows a three-dimensional partial region of the breast. Hence, an effective atomic number Zeff=6 is designed, which is close to a composite organization having a rate of fat v.s., mammary gland=50% and 50% which is present in the human tissue. This composite organization is supposed to be located at the ROI portion of the breast and is one or more types of elements.

Then the processor 35 specifies the positions of one or more pixels which compose the ROI (step S27), and designates an initial pixel position P (step S28).

From the first storage area 33B (or the second storage area 33C) of the ROM 33, the processor 35 reads, for each of the three energy bins, information about calculating a beam hardening correction curve corresponding to the initial effective atomic number Zeff=6 calculated and saved in the foregoing preprocess (step S13) (step S29). This information is expressed by i) the beam hardening correction functions for the effective atomic number $Z_{eff}=7$ designated in the preprocess, which are exemplified in FIG. 13, ii) the biquadratic fitting function f(ρt), and iii) the fitting coefficients $M_j$ (dependent on the atomic number Z) corresponding to the initial effective atomic number $Z_{eff}=6$ designated currently.

Then, using the read information for the beam hardening correction, the beam hardening correction curves corresponding to the currently designated initial effective atomic number $Z_{eff}=6$ are calculated based on the formula (1) (step S30). When referring to the example shown in FIG. 13, the thus-calculated beam hardening correction curves are shown by a reference symbol $CV_{Zeff=6}$ among the various correction curves for each of the three energy bins: $Bin_{Low}$, $Bin_{Middle}$ and $Bin_{High}$. By the way, in those curves, a reference symbol $CV_{Zeff=7}$ indicates a beam hardening correction curve for the effective atomic number $Z_{eff}=7$, while a reference symbol $CV_{Zeff=8}$ indicates a beam hardening correction curve for the effective atomic number $Z_{eff}=8$ On completion of reading the beam hardening correction curves $CV_{Zeff=6}$ for each energy bin, the measured values (i.e., counts) at the first pixel to be treated are beam-hardening corrected in every energy bin (step S31). Specifically, based on the correction curves $CV_{Zeff=6}$ and the target curve $CV_{target}$ for the elements having all the effective atomic numbers Zeff generalized within the desired range of atomic numbers Z=5 to 14 (that is, the common attenuation characteristics of the monochromatic X-rays to elements having the atomic numbers Z=5 to 14), the measured values (counts) are subjected to the beam hardening correction in the respective energy bins. The corrected attenuation amounts are then saved in the image memory 36.

Figure 13:
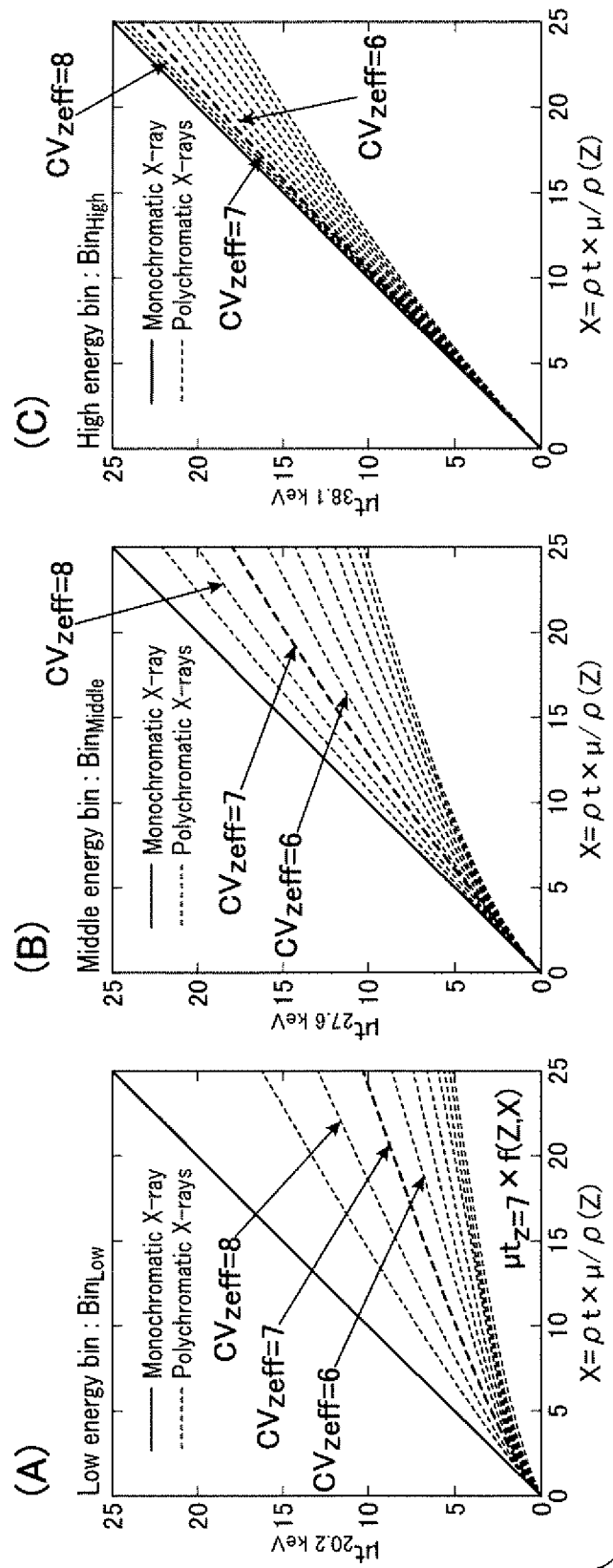
FIG. 13 shows graphs each exemplifying, in each of the energy bins, a target function (a linear line of X=Y) and the generalized beam hardening correction curves.

How to correct the beam hardening is illustrated in FIG. 16, in which the dimensions of both the horizontal and vertical axes are the same as those of FIG. 13. Both figures assign the dimension of the X-ray attenuation amount μt to the vertical axis. When it is assumed that this vertical axis expresses a count value (a count) $μt_n$ (having the dimension of the attenuation amount) at the first axis in the lower energy bin: $Bin_{Low}$, this count value $μt_n$ has influenced by the beam hardening phenomenon. That is, the influence is shown by a positional difference between points $P_{actual}$ and $P_{target}$, in which the count value $μt_n$ Intersects the beam hardening correction curve $CV_{Zeff=6}$ at the point $P_{actual}$ and the count value $μt_n$ intersects the target curve $CV_{target}$, thereby showing a reduction of Δμt in the count value $μt_n$. This difference Δμt expresses an attenuation amount which should be corrected to an ideal state of Δμt=0. In general, this difference Δμt becomes larger as the X-ray energy shifts to its lower energy side.

To cope with this influence, the processor 35 virtually expresses in the memory a two-dimensional graph shown in FIG. 16, for each of the energy bins, and uses the date of the two curves $CV_{Zeff=6}$ and $CV_{target}$ to calculate a corrected value $μt_{Low}$ ($μt_{Middle}$, $μt_{High}$) corresponding to the count value $μt_n$. This calculation can be performed by estimating an intersection point $P_{target}$ with the curve $CV_{target}$, as illustrated in FIG. 16 or estimating a corrected value based on a ratio between the count value $μt_n$ and the difference $Δμt_n$.

The beam hardening correction can therefore be performed, by which beam-hardening corrected count values $μ_{Low}t$, $μ_{Middle}t$, and $μ_{High}t$ at the first pixel designated in the ROI, in each of the three energy bins: $Bin_{Low}$, $Bin_{Middle}$ and $Bin_{High}$. These calculated values are once saved in the image memory 36, for example. The saved data in the memory 36 can be illustrated as in a table (A) of FIG. 17.

The processor 35 uses corrected count values $μ_{Low}t$, $μ_{Middle}t$ and $μ_{High}t$ to normalize these values (step S32). This normalization process is performed every pixel using the following formula.

[Number 1]

$$μ_{High-nor} = \frac{μ_{High}t}{\sqrt{(μ_{High}t)^2 + (μ_{Middle}t)^2}} = \frac{μ_{High}}{\sqrt{μ_{High}^2 + μ_{Middle}^2}} \quad (4')$$

[Number 2]

$$μ_{Low-nor} = \frac{μ_{Low}t}{\sqrt{(μ_{Low}t)^2 + (μ_{Middle}t)^2}} = \frac{μ_{Low}}{\sqrt{μ_{Low}^2 + μ_{Middle}^2}} \quad (4)$$

To be specific, of the three energy bins: $Bin_{Low}$, $Bin_{Middle}$ and $Bin_{High}$, attenuation amount $μ_{Middle}t$ and $μ_{High}t$ of two bins: $Bin_{Middle}$ and $Bin_{High}$ on a higher energy side are used for the normalization. Hence, from the formula (4'), a factor depending on a length of an X-ray path through the object OB (that is, a thickness of the object) is removed, thereby providing an attenuation amount $μ_{High-nor}$ which is independent of the thickness t. Similarly, attenuation amounts $μ_{Low}t$ and $μ_{Middle}t$ of two bins: $Bin_{Low}$ and $Bin_{Middle}$ on a lower energy side are used for the normalization. Hence, from the formula (4"), an attenuation amount $μ_{low-nor}$ which is independent of the thickness t is provided.

The thus-normalized attenuation amounts $μ_{High-nor}$ and $μ_{Low-nor}$ are also saved in the image memory 36, for each of the pixels forming the ROI (refer to a table (B) of FIG. 17).

Then, it is determined by the processor 35 whether or not the beam hardening correction has been completed at all the pixels forming the ROI so that their pixel values (that is, their attenuation amounts are corrected properly (step S33). If it is determined NO at this determination step, it is recognized that there still remain one or more pixels which should be subjected to the beam hardening correction, thereby updating a pixel flag (not shown) and then repeating the tasks at steps S31 and S32. This repetition allows all the pixels of the ROI to be subjected to the beam hardening correction and normalization. As a consequence, at each of the pixels, there can be provided the three count values $μ_{Low}t$, $μ_{Middle}t$ and $μ_{High}t$ corrected by every energy bin and the two attenuation amounts $μ_{High-nor}$ and $μ_{Low-nor}$ normalized according to the high and low energy amounts. These values are also saved in the image memory 36.

In contrast, when determining YES at step S33, the processor 35 recognizes completion of both the beam hardening correction and normalization at all the pixels forming the ROI. This recognition is followed by estimation of an effective atomic number $Z_{eff}$.

Figure 18:
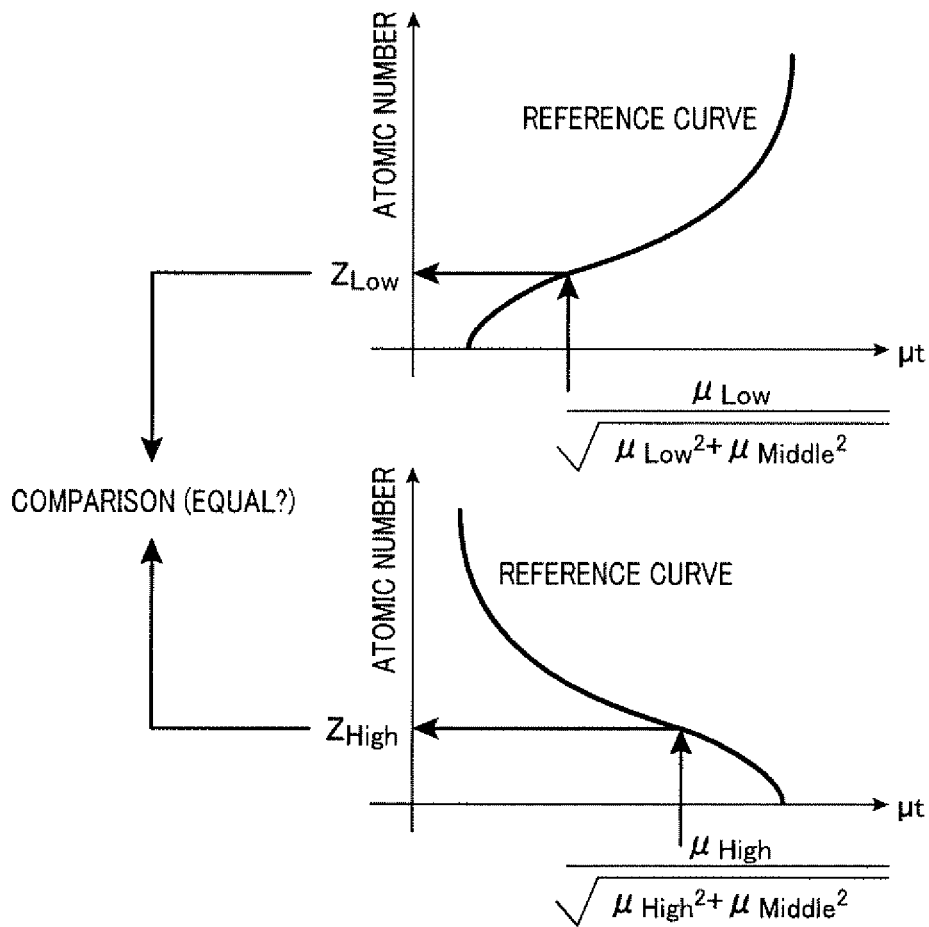
FIG. 18 is an illustration explaining i) how to estimate effective atomic numbers $Z_{High}$ and $Z_{Low}$ on lower and higher X-ray energy sides based on an attenuated X-ray amount normalized at each pixel and ii) mutual comparison of the estimation from both sides.

Practically, the processor 35 reads and store, into its work area, reference curves defining relationships of the "attenuation amounts v.s., an atomic number" which have been previously theoretically calculated and saved in the ROM (step S34). The reference curves, which are exemplified in FIG. 18, show the relationships on attenuation amounts theoretically calculated based on X-ray transmission data collected by radiating the continuous X-rays to a material whose atomic number is known. In the case where the three energy bins are set, there are prepared two non-linear curves, regarding each of the two linear attenuation amounts $μ_{High-nor}$ and $μ_{Low-nor}$, as shown in upper and lower graphs in FIG. 18. Such non-linear curves consist of one non-linear curve in which the atomic number increases as the coefficient ratio increases non-linearly in the graph (as illustrated in the upper graph of FIG. 18), and the other non-linear curve in which, in the opposite way to the above, the atomic number increases as the coefficient ratio decreases non-linearly in the graph (as illustrated in the lower graph of FIG. 18). How to calculate these reference curves based on the linear attenuation amounts is proposed by a research paper "Kimoto, N. et al., 2017, Appl. Radiat. Isot.124".

The processor 35 then uses the foregoing two reference curves based on the two linear attenuation amounts $\mu_{High\text{-}nor}$ and $\mu_{Low\text{-}nor}$ to estimate two atomic numbers $Z_{High}$ and $Z_{Low}$, respectively (step S35). More practically, of the two linear atomic numbers $Z_{High}$ and $Z_{Low}$, the linear attenuation amount $\mu_{High\text{-}nor}$ is applied to the higher-energy reference curve (in the upper graph in FIG. 18), so that an estimated atomic number $Z_{High}$ in the higher energy side can be obtained. In the same way, the linear attenuation amount $\mu_{Low\text{-}nor}$ is applied to the as lower-energy reference curve (in the lower graph in FIG. 18), so that an estimated atomic number $Z_{Low}$ in the lower energy side can be obtained. Both the estimated atomic numbers $Z_{High}$ and $Z_{Low}$ are saved in the image memory 36 (as shown in a table (C) of FIG. 17).

The process at step S35 is performed for each of the pixels forming the ROI interactively designated.

The processor 35 then proceeds to make comparison between the estimated atomic numbers $Z_{High}$ and $Z_{Low}$, every pixel, and determination of whether or not those estimated atomic numbers are equal (step S36). Hence, when it is determined that the estimated atomic numbers $Z_{High}$ and $Z_{Low}$ are equal or regarded as being equal (e.g. a difference between those numbers is below a preset threshold (YES at step S36), it is able to conclude that both the atomic numbers, which are equal to ($Z_{High}=Z_{Low}$), shows an effective atomic number $Z_{eff}$, thus being saved (step S37; refer to a table (D) in FIG. 17).

By contrast, when the determination at step S36 is NO, it is recognized that the atomic numbers $Z_{High}$ and $Z_{Low}$ are not equal or cannot be regarded as being consistent in number to each other. This case means that the foregoing fitting coefficients $M_j$ used for the beam hardening correction are not proper. Moreover, the effective atomic number of an element which is present at a pixel to be processed currently is shifted far from the effective atomic number $Z_{eff}=6$ designated currently as the initial value, whereby the obtained number is unacceptable.

In cases where the determination reveals the inequality between the atomic numbers, the processor 35 designates, again, for example, an effective atomic number $Z_{eff}=7$ which has been prepared for the next, and reads fitting coefficients $M_j$ previously assigned to this newly designated effective atomic number (step S38).

In this update process, of course, an atomic number prepared as a number having a preset-step decimal point, such as an effective atomic number $Z_{eff}=6.5$, can also be designated. In such a modification, the processor 35 can read fitting coefficients $M_j$ corresponding to the effective atomic number $Z_{eff}=7$, and, as an example, calculate a proportional division between the fitting coefficients $M_j$ for $Z_{eff}=7$ and those already owned for $Z_{eff}=6$ so that fitting coefficients $M_j$ for the effective atomic number $Z_{eff}=6.5$ is estimated and used in the same as mentioned.

In a case where the new fitting coefficients $M_j$ assigned to the effective atomic number $Z_{eff}=7$ or 6.5 are obtained, processing according to the same way as the foregoing (steps S30, S31, S32 and S35) is performed. And, every energy bin and every pixel, calculating the beam hardening correction curves, the beam hardening correction in every energy bin and at every pixel, the normalization process, and estimating an effective atomic number are performed in sequence (steps S39, S40, S41 and S42).

As a result, as step S40, the newest attenuation amounts which have been subjected to the beam hardening correction every energy bin and every pixel are updated and saved.

Then, the processing is returned to step S36, at which the foregoing equality determination is performed again. If this determination is NO (i.e., inconsistency), the foregoing steps S38 to S42 are repeated until both the atomic numbers $Z_{High}$ and $Z_{Low}$ become equal or can be regarded as being equal. Hence, within the previously designated range of atomic numbers Zmin to Zmax (for example, Z=5 to 14), an effective atomic number $Z_{eff}$ is finally decided for each of the pixels to be treaded.

After the process at step S37, the processor 35 determines so whether or not deciding the effective atomic number Zeff has been completed for all the pixels forming the ROI (or all pixel areas each formed by combined one or more pixels) (step S43). When this determination is No, the process at step S34 and its subsequent steps are repeated for the next pixel, via a command issued at step S44. In as this way, for all the pixels, the effective atomic number Zeff can be obtained which can understood as an average value of atomic numbers of one or more elements which are present in the X-ray flux path incoming each of the pixels. If needed, this number is updated and saved (refer to the table (D) of FIG. 17).

As described, the atomic number itself is inherent to a substance, but how much the substance having the same atomic will be affected by the beam hardening depends on amounts of energy of the X-ray photons. For this reason, when the atomic number of a substance is decided based on linear attenuation coefficients in only a particular energy bin, deciding the atomic number is likely to be erroneous, thus resulting in a poor beam hardening correction in its accuracy. Hence, as described, the linear attenuation amounts each generalized in each of the higher and lower energy ranges are obtained and a difference between the two attenuation amounts is processed into a value usable to estimate the atomic number as to its true number or a number which can be regarded as the true value, thus providing a higher-accurate estimated effective atomic number $Z_{eff}$.

Then, the processor 35 reads from the image memory 36 the estimated effective atomic numbers $Z_{eff}$ for the respective pixels of the ROI, and uses the read numbers (for example, $Z_{eff}=6$, 6.5, 6.5, 7, 7.2, 7.1, 6, . . . ; read every pixel) to produce an effective atomic number image $IM_{Zeff}$ encoded in a gray scale or colors (step S45). Further, the processor 35 presents this image $IM_{Zeff}$ on the foregoing image (refer to FIG. 14) displayed on the display unit 38 in a superposed manner and save such image data in the memory 36 (step S46).

Figure 19:
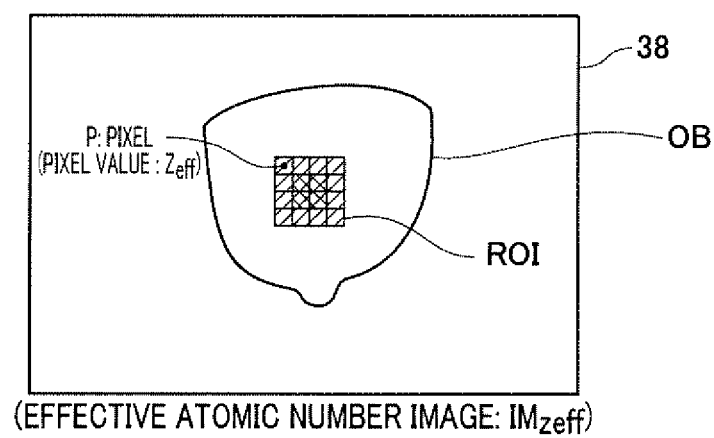
FIG. 19 is a pictorial illustration showing an effective atomic number image produced based on X-ray attenuation amounts beam-hardening corrected at each pixel and exemplifying display thereof.

This image display is pictorially shown in FIG. 19. The background image of this image $IM_{Zeff}$ may be other than a focused image produced by the tomosynthesis technique or the effective atomic number image $IM_{Zeff}$ may be presented alone.

As described, in the present embodiment, as long as the generalized target function(s) and the information about residual errors of an effective atomic number designated in a preset range of effective atomic numbers are obtained, the foreign processing steps enable calculation of the beam hardening correction functions. Accordingly, when the preset range of effective atomic numbers is set to be wider, an amount of calculation for the beam hardening correction functions is not so much larger in comparison with a calculation amount proportional to a size of the range. In other words, in a case where a substance whose elements have a wider range of effective atomic numbers Zeff, the beam hardening correction can be applied to such a substance, with less calculation amounts.

In addition, the previously prepared reference information can be used to obtain an effective atomic number which can be regarded as a true number or a number close to the true number, based on the effective atomic numbers ($Z_{Low}$ and $Z_{High}$) estimated in the lower and higher energy range sides. The effective atomic number images of substances can be produced with high accuracy. This results in that the types and/or states of substances in the X-ray paths can be determined reliably.

Moreover, in the present embodiment, the beam hardening correction is carried out for each of the pixels. This beam hardening correction includes not only correction for a narrowly defined beam hardening phenomenon but also broadly defined correction for removing or reducing errors in count values in which various error factors are included, such as X-ray attenuation due to a heel effect or others, and/or errors due to circuit factors such as charge sharing. It is therefore possible to provide highly accurate correction as if the count values have been calibrated from the beginning, i.e., at a time when transmitted X-rays are detected by the detector. Hence, the processing can be performed stably and accurately, when the count values are used for image reconstruction or object analysis. In addition, in identifying types and/or states of substances based on the measurements, accuracy of the identification can be raised.

Second Embodiment

Referring to FIGS. 20 to 24, a second embodiment of the X-ray apparatus according to the present invention will now be described.

This X-ray apparatus is related to another application of the measurements which have been subjected to the beam hardening correction performed in the foregoing first embodiment. In order to omitting or simplifying the descriptions, the elements which are the same or similar as or to those described in the first embodiment will be given the same reference numbers or symbols.

In the present embodiment, X-ray images can be provided with various modes produced by the final measurements outputted every energy bin and subjected to the beam hardening correction. Practically, when the flow processing shown in FIG. 4 has been completed, the measurements corrected in the beam hardening at each of the targeted pixels (or the pixel areas) in the respective energy bins have already been saved in the image memory 36 via the process as step S40.

Figure 20:
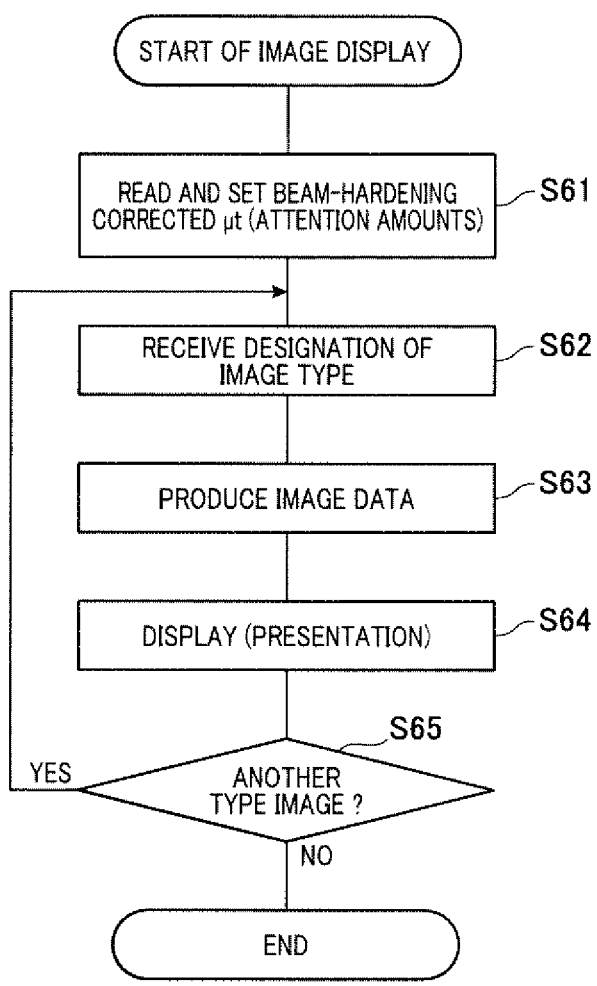
FIG. 20 is a flowchart outlining a process for image display performed in a second embodiment of the present invention, the process being associated with the process flow in the first embodiment.

Thus, the processor 35 reads, from the image memory 36 into the work area, the corrected measurements every energy bin, and finally recognizes that such measurements are for producing X-ray images (FIG. 20, step S61). The confirmed measurements can be pictorially shown as in FIG. 21, for instance, if being developed in a memory. These finally confirmed measurements can be expressed as $\mu_{Low}t$, $\mu_{Middle}t$ and $\mu_{High}t$ for the lower energy bin: $Bin_{Low}$, the middle energy bin: $Bin_{Middle}$, and the higher energy bin: $Bin_{High}$.

Then, the processor 35 decides how X-ray images are displayed (presented) interactively with the operator (step S62). Such X-ray images include not only an optically (best) focused image (including a panoramic image) produced by optically (best) focusing each of the counts counted at the pixels, that is, X-ray attenuation amounts μt using the tomosynthesis technique, but also various images seeing for the qualitative performance of the pixel values acquired by the photon counting. Such photon-counting inherent images include a three-dimensional scatter diagram, an absorption vector length image, and average absorption value image. In this embodiment, the operator can selectively designate, as a default setting or interactively, the optimally focused image, the three-dimensional image, the absorption vector length image, and the average absorption value image. In addition, such images can include an X-ray transmission image produced by coding the X-ray attenuation amounts μt in a gray scale, for instance.

The three-dimensional scatter diagram, the absorption vector length image, and the average absorption value image will now be described briefly.

<Regarding the Three-Dimensional Scatter Diagram>

Figure 22:
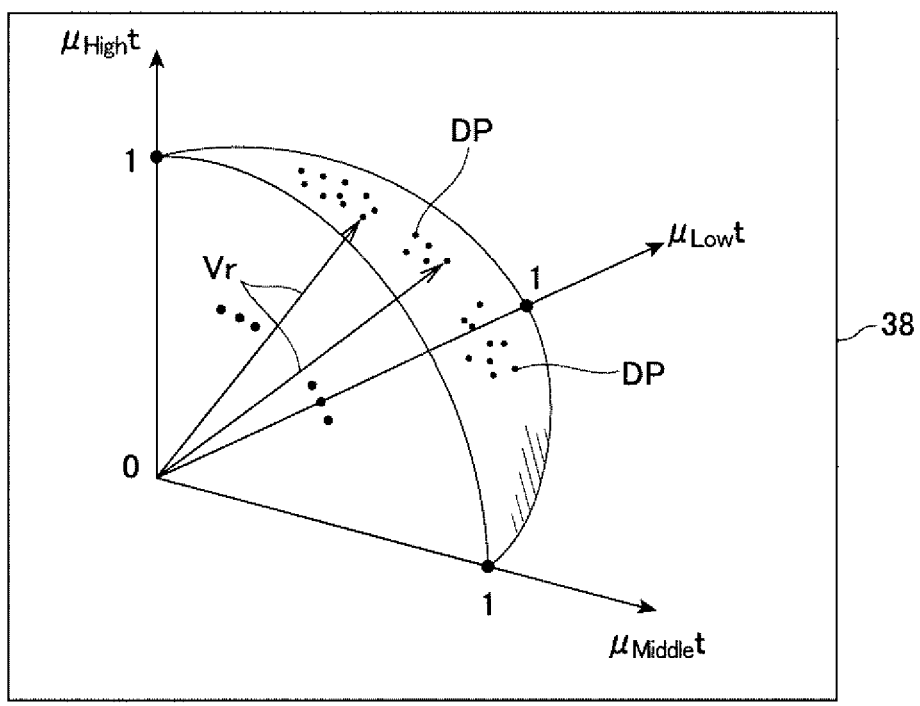
FIG. 22 is a view exemplifying an image inherent to the photon counting detection, which is displayed in the second embodiment.
Figure 23:
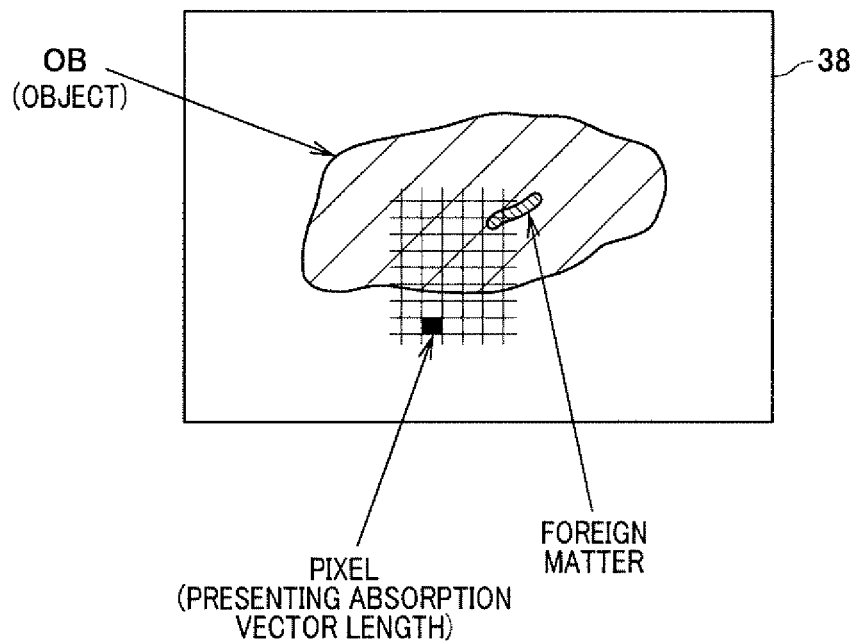
FIG. 23 is a view exemplifying another image inherent to the photon counting detection, which is displayed in the second embodiment.
Figure 24:
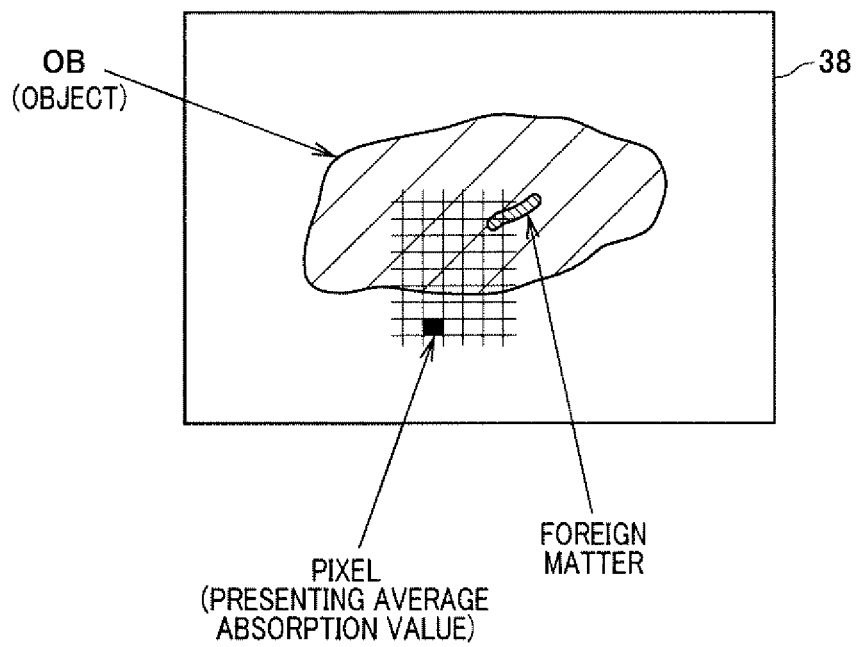
FIG. 24 is a view exemplifying another image inherent to the photon counting detection, which is displayed in the second embodiment.

In the present embodiment, the linear attenuation amounts $\mu_i t$ have three degrees of freedom, because of use of the three X-ray energy bins, $Bin_{Low}$, $Bin_{Middle}$, $Bin_{High}$. Hence, a three-dimensional linear attenuation value vector $$(\mu_{Low}t, \mu_{Middle}t, \mu_{High}t)$$

can be set at each pixel. A length of this vector, that is, a linear attenuation value vector length $$((\mu_{Low}t)^2+(\mu_{Middle}t)^2+(\mu_{High}t)^2)^{1/2}$$

can be used as a denominator in calculating a normalized three-dimensional linear attenuation value vector (herein referred to as a linear attenuation vector) from a formula of:

$$(\mu_{Low}, \mu_{Middle}, \mu_{High})/(\mu_{Low}^2+\mu_{Middle}^2+\mu_{High}^2)^{1/2} \qquad (5)$$

where the factor of the thickness t disappears from this linear attenuation vector. When a three-dimensional Cartesian coordinate system whose three axes are $\mu_{Low}t$, $\mu_{Middle}t$ and $\mu_{High}t$ is set, the three-dimensional linear attenuation vector has a start point at the origin of the three-dimensional coordinate system and an end point on a spherical surface, of which radius is 1. This three-dimensional linear attenuation vector is calculated as each pixel and mapped in the three-dimensional coordinate system, resulting in that the end points are mapped within a certain area around a point mapped on the spherical surface. This area is composed of an aggregation of scattered points mapped with statistical errors. The inventors refer to this three-dimensional scatter-point map as a three-dimensional scatter diagram, which is exemplified in FIG. 22. In FIG. 22, a reference symbol Vr indicates a three-dimensional linear attenuation vector and a reference symbol DP indicates scattered points.

How the end points (scatter points) of the linear attenuation vectors are mapped on the spherical surface, that is, in the three-dimensional scatter diagram, is inherent to the type itself of a substance contained in an object. In other words, the substance type is changed, the scatter points are also changed, which is true from a theoretical viewpoint. These changes are led to identification of types of substances (materials).

<Regarding Absorption Vector Length Image>

Moreover, the vector length at each pixel can be calculated by a formula of:

$$t(\mu_{Low}^2+\mu_{Middle}^2+\mu_{High}^2)^{1/2} \qquad (6)$$

The Inventors refer to this scalar value as an absorption vector length (or a pseudo-absorption value). This absorption vector length can be formed as a two-dimensional image whose pixels are indicated by the absorption vector length. The inventors refer this two-dimensional image as an absorption vector length image (or a pseudo-absorption image), which is pictorially exemplified in FIG. 23.

<Concerning Average Absorption Value Image>

Furthermore, when imaginary average linear attenuation coefficients in the three energy bins: $Bin_{Low}$, $Bin_{Middle}$ and $Bin_{High}$, which are linear attenuation coefficients to effective energy amounts in the respective energy ranges, are expressed by $\mu_{Low}$, $\mu_{Middle}$ and $\mu_{High}$ and an object has a thickness t in an X-ray transmission direction, the pixel value at each of the pixels can be provided based on the following formula:

$$\text{pixel value} = t \cdot (\mu_{Low} + \mu_{Middle} + \mu_{High})/3 \quad (7)$$

or $$\text{pixel value} = t \cdot (a_1\mu_{Low} + a_2\mu_{Middle} + a_3\mu_{High})/3 \quad (8)$$

where $a_1$, $a_2$, $a_3$: weighting coefficients which are 0 or more positive real numbers, and which meet $a_1+a_2+a_3=3$.

That is, the pixel values can be obtained as scaler quantities depending on the thicknesses t. The foregoing formulas have a denominator of 3. The reason for this is to calculate an averaged value over the three energy bins: $Bin_{Low}$, $Bin_{Middle}$ and $Bin_{High}$, that is, all the energy bins.

In the foregoing formula, the weighting coefficients $a_1$, $a_2$, and $a_3$ can be set as default values or can be changed by an operator during operator's work such as Interpretation. The condition for the coefficients, "$a_1+a_2+a_3=3$," is intended to perform weighted average, so that if a pixel value is treated by multiplying the weighted average value by a real number, this condition can be removed.

An image composed of pixels whose pixel values are calculated as stated is defined as an average absorption value image by the present inventors. An example of this average absorption value image is pictorially shown in FIG. 24, in which each of the pixels has a pixel value calculated based on the forgoing formula (7) or (8). As a variation, the pixel value of each pixel may be given as a value calculated from pixel values of definite-number combined pixels surrounding each designated pixel.

The average absorption value image according to the present invention is not always limited to the application in which the three X-ray energy bins are defined in the continuous X-ray spectrum. For example, the number of X-ray energy ranges (bins) may be two, or four or more, according to which the continuous X-ray spectrum is divided depending on energy amounts of the X-rays.

The processor 35 converts the data of the X-ray image designated among the various types of X-ray images listed above, to a predetermined or desired display format (step S63), and displays (presents) the image data on the display unit 38 (step S64).

Then, in an interactively with the operator, the processor 35 determines whether or not another mode of display is required (step S65), and, if necessary, repeats step S63.

As described, in addition to the conventionally known X-ray images, from the measurements whose beam hardened components are accurately corrected, with the superiority of the photon counting still alive, the distinguishing X-ray images, that is, the three-dimensional scatter diagram, absorption vector length image, and average absorption value image can be selected and represented according to a request.

Accordingly, in the present embodiment, the same operational effects obtained in the foregoing first embodiment can also be obtained. Additionally, the X-ray attenuation values whose beam hardening components have been corrected sufficiently can be developed into various X-ray images which have high values in clinical applications. That is, in the X-ray apparatus according to the second embodiment, the advantage of "highly accurately estimating the effective atomic number Zeff results in searching correcting information used for more proper beam hardening correction, which results in deciding pixel values of an image with higher accuracy" gained in the foregoing first embodiment can be utilized effectively. Practically, in addition to providing an image of the foregoing effective atomic numbers $Z_{eff}$, it is also possible to provide three-dimensional scatter diagrams, absorption vector length images and average absorption value images, which are unique and effective in clinical applications. Meanwhile, quantitative performance which should be owned by image pixel values is improved and unevenness among the pixels, caused due to irregulates inherent to detection at the pixels, is also be reduced. The beam hardening correction is also able to absorb fluctuations caused due to a heel effect in the X-ray tube. Accordingly, when these images are used to identify (determine or estimate) types and/or states of substances (elements) composing an object in a highly accurate and stable manner, very useful image information can be provided, which is also effective in clinical applications.

In the foregoing plural embodiments, the whole elements of the data processing apparatus 30 functionally configure a calculation step, a correction step, a normalization step, an estimation step and a equality determining step, and, calculation means, correction means, normalization means, estimation means and equality determining means. Additionally, by the whole elements of the data processing apparatus 30, a preprocess step, first and second correction steps, an attenuation amount processing step and an X-ray image presenting step, and preprocessing means, correction means, attenuation amount processing means, and X-ray image presenting means are functionally configured, which are necessary for the processing in the X-ray apparatus.

<Modifications>

The foregoing embodiments can be modified into various other modes.

First of all, the number of X-ray energy bins is not always to limited to three, but may be set to four or more energy bins by adding energy discriminating thresholds. For example, in the case of setting four energy bins, the two lower energy side bins are used to calculate an effective atomic number $Z_{Low}$ normalized for the lower energy side, while the two higher energy side bins are used to calculate an effective atomic number $Z_{High}$ normalized for the higher energy side, in the same way as the foregoing.

Even in the three energy bins as in the foregoing embodiments, the foregoing preprocess employs a normalization step in which normalized X-ray attenuation amounts in the lower and higher energy sides can be calculated based on the following modified formulae:

$$\mu_{Middle}/(\mu_{Middle}^2+\mu_{High}^2)^{1/2} \text{ and } \mu_{High}/(\mu_{Low}^2+\mu_{Middle}^2)^{1/2}$$

Figure 14:
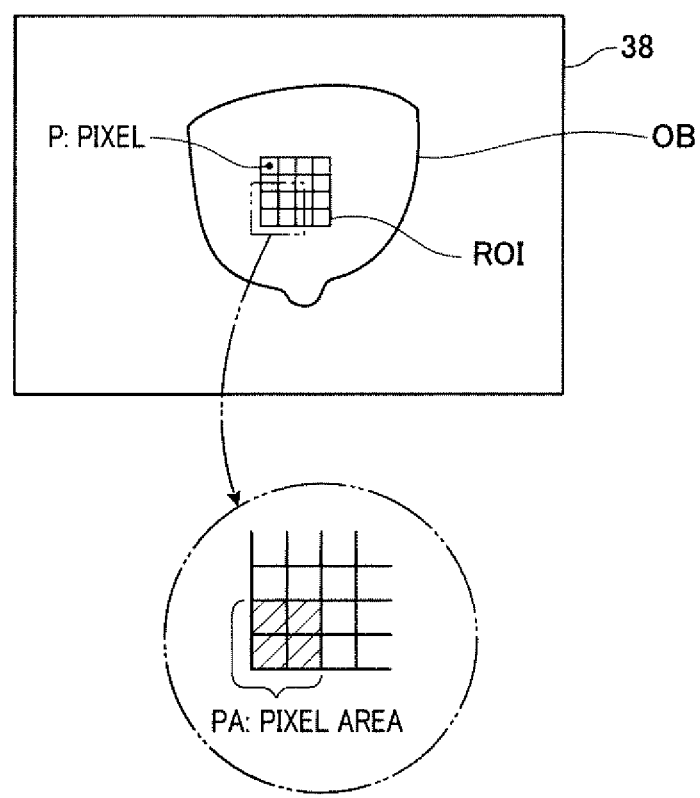
FIG. 14 is a pictorial illustration of an X-ray image in which an ROI is superposed thereon, the ROI setting an area to which the beam hardening correction is applied.

The unit on which the effective atomic number $Z_{eff}$ is calculated not necessarily confined to a unit defined as each of the physical pixels installed in the detection layer of the detector. Pixel signals from a predetermined number of plural pixels are combined, so that, as shown in FIG. 14, it is possible to imaginarily realize a pixel area PA which also serves as a unit for the calculation. In addition, a detector having only one pixel can be adopted in the X-ray apparatus.

The present invention will not be limited to the foregoing configurations, but can be practiced as combinations with various conventionally known modes, as long as the combinations will not depart from the gist of the present invention.

Furthermore, how to obtain the effective atomic number Zeff will not be limited to the foreign calculation method. For example, any one of the atomic numbers $Z_{High}$ and $Z_{Low}$ estimated as step S35 and the effective atomic number Zm designated in performing the beam hardening correction can be compared with each other, so that an effective atomic number $Z_{eff}$ can be calculated.

Figure 25:
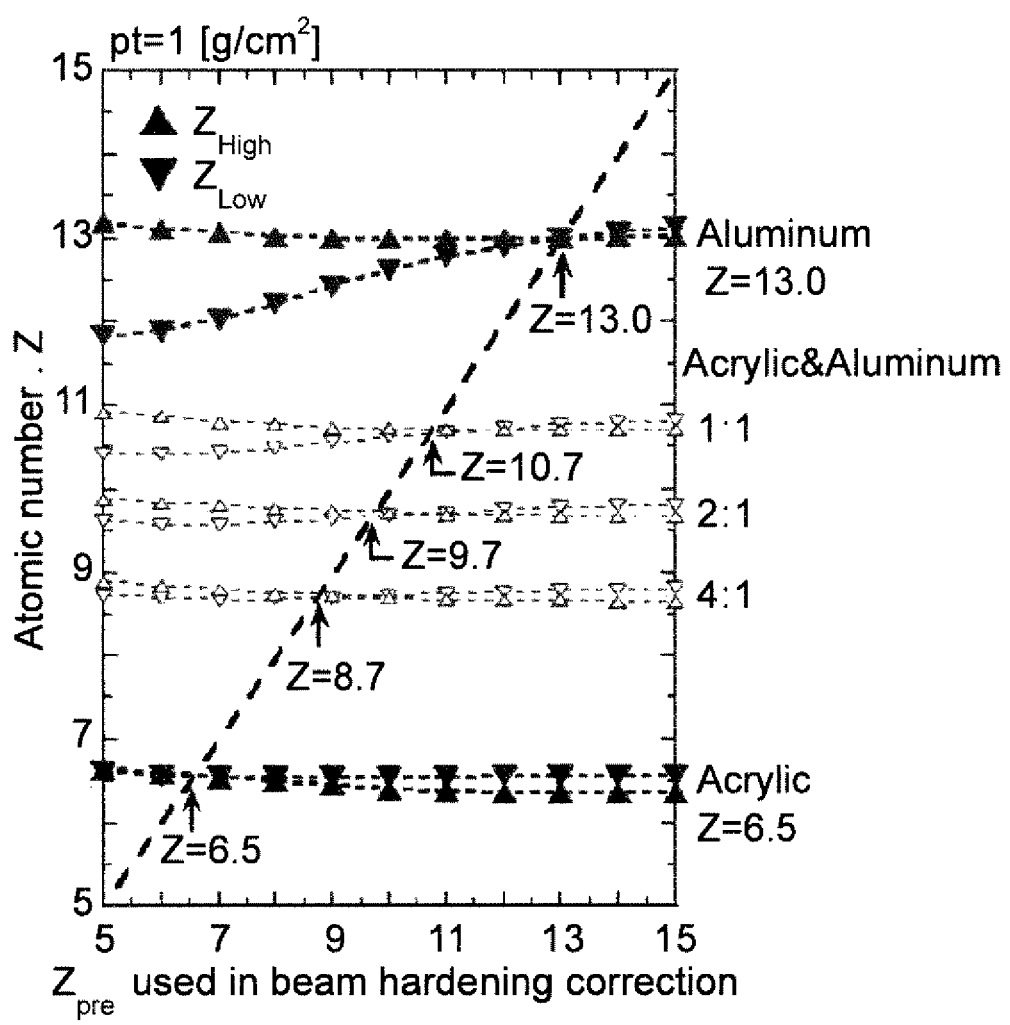
FIG. 25 is a graph exemplifying a relationship among the lower-energy side effective atomic number ($Z_{Low}$), the higher energy side effective atomic number ($Z^{High}$), and effective atomic numbers Zm which are set in advance when the beam hardening correction is performed.

In addition, as exemplified in FIG. 25, when the atomic numbers $Z_{High}$ and $Z_{Low}$ both estimated at step S35 are equal, it was found that both of the atomic numbers $Z_{High}$ and $Z_{Low}$ also agree with the effective atomic number Zm previously designated in the beam hardening correction.

As exemplified in FIG. 25, numerical simulation for substance identification was conducted with a plurality of samples. In this numerical simulation, with changing the effective atomic number Zm (previously designated in the beam hardening correction) from 5 to 15, the effective atomic number $Z_{Low}$ in the lower energy side and the effective atomic number $Z_{High}$ in the higher energy side are calculated and plotted on a graph. As shown in FIG. 25, in a case an object being measured is aluminum (Its effective atomic number is 13.0), curves depicting the numbers $Z_{High}$ and $Z_{Low}$ intersect with each other at a position of Z=13.0. In other words, both the effective numbers $Z_{Low}$ and $Z_{High}$ are equal at the position of Z=13.0. Based on this fact, in conducting the foregoing embodiment, 13.0 is saved as the effective atomic number $Z_{eff}$ (step S37).

As will be clear from FIG. 25, the position at which both the curves $Z_{High}$ and $Z_{Low}$ intersect with each other provides an effective atomic number Zm of 13.0 which is set in advance when the beam hardening correction is performed. To be short, such three values are equal, and $Z_{High}=Z_{Low}=Zm=13.0$ is realized As exemplified in FIG. 25, the same result as the above was also true of an acrylic resin material serving as an object and having an effective atomic number of 6.5. The three numbers agreed with a point showing $Z_{High}=Z_{Low}=Zm=6.5$. A double structure substance consisting of acrylic resin and aluminum showed that there is a point at which three numbers are approximately equal.

Based on the numerically simulated results, at least one of the effective atomic numbers $Z_{Low}$ and $Z_{High}$ in the lower and higher energy sides can be calculated, and the calculated number can be compared with an effective atomic number Zm previously set, whereby the effective atomic number Zeff can be decided. This method is of advantage in terms of an increased processing speed, because it is sufficient to calculate only one of the effective atomic numbers $Z_{Low}$ and $Z_{High}$ in the lower and higher energy sides.

In other words, provided that two or more X-ray energy bins are set, the estimation step enables the X-ray attenuation amounts to be generalized and to estimate at least one effective atomic number. When the at least one effective atomic number is estimated, the correction step enables that estimated number to be compared with an effective atomic number Zm previously designated, thereby deciding an effective atomic number $Z_{eff}$ which is a true effective atomic number.

Alternatively, provided that the three numbers, which are the effective atomic numbers $Z_{Low}$ and $Z_{High}$ in the lower and higher energy sides and the effective atomic number Zm previously set, become equal, the effective atomic number $Z_{eff}$ may be decided. This configuration is effective for increasing accuracy of substance identification.

The number of effective atomic numbers estimated by the estimation step may be three or more, in which, as the number of estimated effective atomic numbers becomes larger, accuracy of substance identification becomes improved, although there is a reduction in the processing speed. By way of example, an increase in the number of estimated effective atomic numbers can be realized by increasing the number of X-ray energy bins which is set in advance. An alternative to this increase is that, from a plurality of X-ray energy bins, bins are selected with various combination, such as selection from the lower energy bin: $Bin_{Low}$ and the higher energy bin: $Bin_{High}$, in order to estimate an effective atomic number based on the sleeted bins. The energy bins can be selected with various combinations, whereby the number of estimated effective atomic numbers can also be increased.

PARTIAL REFERENCE SIGNS LIST

10 X-ray apparatus
21 X-ray generator
22 X-ray tube
24 detector
25 detecting layer
26 data acquisition circuit
30 data processing apparatus (computer)
33 ROM
33A, 33B, 33C storage area
35 processor (CPU is incorporated)
37 input device
38 display unit
P pixel
PA pixel area
OB object

The invention claimed is:

1. A method of processing data of count values, the count values being provided by radiating beam-formed X-rays having a continuous X-ray spectrum to an object, detecting the X-rays transmitted through the object, and counting, as the count values, photons of the X-rays in each of two or more preset X-ray energy bins and in each of pixel areas each consisting of one or more pixels, the method comprising:

a calculation step calculating, in each of the X-ray energy bins and at each of the pixel areas, count data indicated by a ratio between the count values obtained with no object and with the object;

a correction step performing beam hardening correction with the count data at each of the pixel areas and in each of the X-ray energy bins to obtain X-ray attenuation amounts (μt: μ denotes a linear attenuation coefficient and t denotes a thickness of the object in a projection direction of the X-rays in the object), based on correcting information according to a preset effective atomic number, the beam hardening correction correcting a beam hardening phenomenon caused when the X-rays are transmitted through the object;

a normalization step normalizing the X-ray attenuation amounts in each of two of the X-ray energy bins, selected from the two or more X-ray energy bins, to obtain, at each of the pixel areas, at least one normalized X-ray attenuation amounts;

an estimation step estimating at least one effective atomic number from reference information showing a theoretical relationship between the normalized X-ray attenuation amounts and an effective atomic number of an element; and an equality determining step determining whether or not at least two effective atomic numbers are mutually compared to determine that the at least two effective atomic numbers are equal or are regarded as being equal, the at least two effective atomic numbers being designated among the at least one effective number estimated by the estimation step and the effective atomic number preset by the correction step.

2. The processing method of claim 1, wherein
the X-ray energy bins are previously set and three or more in number, and
the normalization step obtains the two or more normalized X-ray attention amounts in a state where combinations of the two X-ray energy bins selected from the X-ray energy bins are different.

3. The processing method of claim 2, wherein
the estimation step obtains two or more effective atomic numbers from the two or more normalized X-ray attenuation amounts obtained by the normalization step; and
the equality determining step makes comparison between two or more effective atomic numbers consisting of i) the two or more effective atomic numbers obtained by the estimation step and ii) the effective atomic number preset for the correction step.

4. The processing method of claim 1, wherein
the equality determining step includes
a calculation step calculating a difference between two numbers selected among atomic numbers consisting of i) the one or more effective atomic number estimated by the estimating step and ii) the effective atomic number preset for the correction step; and
a difference determining step determining whether or not the difference is equal to or smaller than a predetermined threshold.

5. The processing method of claim 4, characterized in that the processing method includes
a presentation step presenting, in each of the X-ray energy bins and at each of the pixel areas, that two effective atomic numbers selected from effective atomic numbers consisting of i) the one or more effective atomic numbers obtained by the estimation step and ii) the effective atomic number preset for the correction step are regarded as being equal or approximately equal, and the equal or approximately equal number is a true effective atomic number or an approximately true effective number, when difference determining step determines that the difference is equal to or smaller than the predetermined threshold.

6. The processing method of claim 1, wherein the pixel areas each is an area consisting of a single pixel.

7. The processing method of claim 1, wherein
the X-ray energy bins are three X-ray energy bins consisting of a lower energy bin, a middle energy bin, and a higher energy bin which are mutually adjunct in an energy spectrum of the X-rays;
the two energy bins on the lower energy side consists of the lower energy bin and the middle energy bin; and
the two energy bins on the higher energy side consists of the middle energy bin and the higher energy bin.

8. The processing method of claim 1, wherein
the X-ray energy bins are four or more X-ray energy bins which are mutually adjacent or discrete in an energy spectrum of the X-rays;
two energy bins on the lower energy side consist of two energy bins mutually different on the lower energy side; and
two energy bins on the higher energy side consist of two energy bins mutually different on the higher energy side.

9. An apparatus of processing data of count values, the count values being provided by radiating beam-formed X-rays having a continuous X-ray spectrum to an object, detecting the X-rays transmitted through the object, and counting, as the count values, photons of the X-rays in each of two or more preset X-ray energy bins and in each of pixel areas each consisting of one or more pixels, the apparatus comprising:
calculation means calculating, in each of the X-ray energy bins and at each of the pixel areas, count data indicated by a ratio between the count values obtained with no object and with the object;
correction means performing beam hardening correction with the count data at each of the pixel areas and in each of the X-ray energy bins to obtain X-ray attenuation amounts ($\mu t$: $\mu$ denotes a linear attenuation coefficient and t denotes a thickness of the object in a projection direction of the X-rays in the object), based on correcting information according to a preset effective atomic number, the beam hardening correction correcting a beam hardening phenomenon caused when the X-rays are transmitted through the object;
normalization means normalizing the X-ray attenuation amounts in each of two of the X-ray energy bins, selected from the two or more X-ray energy bins, to obtain, at each of the pixel areas, at least one normalized X-ray attenuation amounts;
estimation means estimating at least one effective atomic number from reference information showing a theoretical correspondence relationship between the normalized X-ray attenuation amounts and an effective atomic number of an element; and
equality determining means determining whether or not at least two effective atomic numbers are mutually compared to determine that the at least two effective atomic numbers are equal or are regarded as being equal, the at least two effective atomic numbers being designated among the at least one effective number estimated by the estimation means and the effective atomic number preset by the correction means.

10. A method of processing data of count values, the count values being provided by radiating beam-formed X-rays having a continuous X-ray spectrum to an object, detecting the X-rays transmitted through the object, and counting, as the count values, photons of the X-rays in each of two or more preset X-ray energy bins and in each of pixel areas each consisting of one or more pixels, the method comprising:
a preprocessing step previously preparing, for each of the X-ray energy bins, correcting information based on characteristics showing i) both mass thicknesses pt of a plurality of types of substances whose atomic numbers are known and ii) an X-ray attenuation amount $\mu t$ ($\mu$: a linear attenuation coefficient and t: a thickness of the object in an X-ray path direction passing through the object) at an effective energy among in each of the X-ray energy bins, the correcting information being for correcting X-ray count values subjected to a beam hardening phenomenon when the X-rays are transmitted through the object; and an attenuation amount processing step processing by applying the correcting information, prepared by the preprocessing step, to the X-ray count values for the beam hardening correction at each of the pixel areas to finally decide the X-ray attenuation amounts and processing the decided X-ray attenuation amounts, wherein
the attenuation amount processing step comprises:
an X-ray image producing step producing a photon counting X-ray image based on the X-ray attenuation amounts corrected and finally decided by the correction step; and
an X-ray image presenting step presenting the produced X-ray image,
wherein
the preprocessing step comprises:
a step setting a desired range (Zmin to Zmax) of effective atomic numbers of elements composing compositions of the object;
a step theoretically estimating a graph of respective effective atomic numbers in a two-dimensional coordinate having a horizontal axis and a vertical axis, wherein the horizontal axis is assigned to a mass thickness (ρt) of an element and the vertical axis is assigned to a linear attenuation amount (μt: μ denotes a linear attenuation coefficient of the element, t denotes a thickness of the object in an X-ray path direction) at an effective energy amount in each of the X-ray energy bins, the element having a plurality of effective atomic numbers selected discretely from an effective atomic number in the desired range of the effective atomic numbers (Zm), the plurality of effective atomic numbers including a lower limit and an upper limit of the desired range;
a step designating a desired effective atomic number (Zm=7) from the effective atomic numbers belonging to the desired range (Zmin to Zmax);
a step setting a linear target ruction in the two-dimensional coordinate when assuming that monochromatic X-rays are radiated to the object composed of the element having the designated effective atomic number;
a step generalizing, in the two-dimensional coordinate, by multiplying the horizontal axis direction by a gradient (μ/ρ) of the target function to generalize a plurality of curves provided by the plurality of effective atomic numbers as a variable of the effective atomic numbers; and
a step designating a curve of the element having the designated effective atomic number among the plurality of generalized curves, and, before correcting the beam hardening, saves, into a storage, beam hardening correction functions as the correcting information based on residual errors between the designated curve and the other curves, the beam hardening correction functions being for correcting the beam hardening.

11. The processing method of claim 10, wherein the attenuation amount processing step comprises a correction step,
wherein
the correction step that reads, from the storage, data indicating the corrected beam hardening correction function and performs the correction of the count values.

12. The processing method of claim 10, wherein
the attenuation amount processing step includes
a calculation step calculating, in each of the X-ray energy bins and at each of the pixel areas, count data indicated by a ratio between the count values obtained with no object and with the object;
a first step reading, from the storage, as the correcting information, the beam hardening correction function corresponding to the desired effective atomic number and, based on the read beam hardening correcting information, applying the beam hardening correction to the count data, at each of the pixel area and in each of the X-ray energy bins to obtain X-ray attenuation amounts (μt: μ denotes a linear attenuation coefficient and t denotes a thickness of the object in a projection direction of the X-rays in the object);
a normalization step normalizing the X-ray attenuation amounts in two of the X-ray energy bins selected from two or more bins among the X-ray energy bins to obtain, at each of the pixel areas, one or more genialized X-ray attenuation amounts;
an estimation step estimating, at each of the pixel area, one or more effective atomic number based on reference information showing a theoretical correspondence relationship between the normalized X-ray attenuation amount and effective atomic numbers of the elements;
an equality determining step determining whether or not an equality degree is in an allowable range thereof, by making comparison between two or more effective atomic numbers designated among atomic numbers consisting of i) the one more effective atomic numbers estimated by the estimation step and ii) the effective atomic number preset for the first correction step; and
an estimation step estimating that, when the equality determining step determines that the equality degree is within the allowable range, an effective atomic number presenting the determined equality is a true effective atomic number (Zeff) at each of the pixel areas.

13. The processing method of claim 12, wherein
the attenuation amount processing step includes
a correcting information accruing step acquiring the correcting information obtained when two atomic numbers selected among i) the one or more effective atomic numbers estimated by the estimation step and ii) the effective atomic number preset for the first correction step are equal or regarded as being equal;
an attenuation amount deciding step deciding, as a final X-ray attenuation amount at each of the pixel areas, the X-ray attenuation amounts (μt) corrected with the correcting information by the first correction step; and
an image presenting step presenting an X-ray image under photon-counting of the object, based on the X-ray attenuation amounts of the pixel area finally decided by the attenuation amount deciding step.

14. The processing method of claim 12, wherein
the attenuation amount processing step includes a step of producing the effective atomic number image from the effective atomic numbers estimated by the estimation step.

15. The processing method of claim 12, wherein
the attenuation amount processing step includes
a second correction step reading, from the storage, a further beam hardening correcting function corresponding to a further effective atomic number, as the correcting information, and applying the beam hardening correction to the count data based on the further beam hardening correcting function, at each of the pixel areas and for each of the energy bins, to obtain the X-ray attenuation counts, when the equality determining step determines that the equality degree is not within the allowable range; and a repletion commanding step repeatedly commanding, one or more times, the normalization step, the estimation step, and the equality determining step successively from the second correction step.

16. The processing method of claim 13, wherein
the second correction step calculates the correcting information provided by a proportional division of the residual errors depending on a selected value between the effective atomic number read before and an effective atomic number discretely adjacent to the effective atomic number read before, when the further beam hardening correction function is read.

17. The processing method of claim 12, wherein
the beam hardening correction function based on the residual errors is expressed by a biquadratic function, wherein
the biquadratic function is expressed by $$f(\rho t)=a_0+a_1\times(\rho t)+a_2\times(\rho t)^2+a_3\times(\rho t)^3+a_4\times(\rho t)^4$$

wherein $a_0, a_1, a_2, a_3$ and $a_4$ ($a_j$(j=0 to 4)) are coefficients which are expressed by $$a_0=M_0+M_1\times Z+M_2\times Z^2+M_3\times Z^3+M_4\times Z^4$$

$$a_1=M_0+M_1\times Z+M_2\times Z^2+M_3\times Z^3+M_4\times Z^4$$

$$a_2=M_0+M_1\times Z+M_2\times Z^2+M_3\times Z^3+M_4\times Z^4$$

$$a_3=M_0+M_1\times Z+M_2\times Z^2+M_3\times Z^3+M_4\times Z^4$$

$$a_4=M_0+M_1\times Z+M_2\times Z^2+M_3\times Z^3+M_4\times Z^4$$

wherein Z denote the effective atomic number and $M_j$(j=0 to 4) denote coefficients.

18. The processing method of claim 12, wherein
the beam hardening correction function based on the residual errors is expressed by a high-dimensional function of the mass thickness ($\rho t$) which has coefficients "a" expressed by a high-dimensional function of the effective atomic number Z.

19. The processing method of claim 12, wherein
the attenuation amount processing step includes
a display step displaying on a monitor images based on the count values; and
a pixel setting step displaying a region of interest (ROI) on the monitor and setting, as the pixel area, each of pixels forming the region of interest.

20. The processing method of claim 12, wherein
the attenuation amount processing step includes
a display step displaying on a monitor an image based on the count value; and
a pixel setting step displaying on the monitor a region of interest (ROI) and, of pixels forming the region of interest, setting one or more groups of mutually adjacent and combined pixels as each of the pixel areas.

21. The processing method of claim 12, wherein
the equality determining step includes
a calculation step calculating a difference between two numbers selected among atomic numbers consisting of i) the one or more effective atomic number estimated by the estimating step and ii) the effective atomic number preset for the correction step; and
a difference determining step determining whether or not the difference is equal to or smaller than a predetermined threshold.

22. The processing method of claim 21, wherein the processing method includes
a presentation step presenting, in each of the X-ray energy bins and at each of the pixel areas, that two effective atomic numbers selected from effective atomic numbers consisting of i) the one or more effective atomic numbers obtained by the estimation step and ii) the effective atomic number preset for the correction step are regarded as being equal or approximately equal, and the equal or approximately equal number is a true effective atomic number or an approximately true effective number, when difference determining step determines that the difference is equal to or smaller than the predetermined threshold.

23. The processing method of claim 10, wherein
the two or more X-ray energy bins are three X-ray energy bins consisting of a lower energy bin, a middle energy bin, and a higher energy bin which are mutually adjacent in an energy spectrum of the X-rays;
the two energy bins on the lower energy side consists of the lower energy bin and the middle energy bin; and
the two energy bins on the higher energy side consists of the middle energy bin and the higher energy bin.

24. The processing method of claim 10, wherein
the two or more X-ray energy bins are four or more X-ray energy bins which are mutually adjacent or discrete in an energy spectrum of the X-rays;
two energy bins on the lower energy side consists of two energy bins mutually different on the lower energy side; and
two energy bins on the higher energy side consists of two energy bins mutually different on the higher energy side.

25. An X-ray apparatus for processing data of count values, the count values being provided by radiating beam-formed X-rays having a continuous X-ray spectrum to an object, detecting the X-rays transmitted through the object, and counting, as the count values, photons of the X-rays in each of two or more preset X-ray energy bins and in each of pixel areas each consisting of one or more pixels, the X-ray apparatus comprising:
preprocessing means previously preparing, for each of the X-ray energy bins, correcting information based on characteristics showing i) both mass thicknesses $\rho t$ of a plurality of types of substances whose atomic numbers are known and ii) an X-ray attenuation amount $\mu t$ ($\mu$: a linear attenuation coefficient and t: a thickness of the object in an X-ray path direction passing through the object) at an effective energy among in each of the X-ray energy bins, the correcting information being for correcting X-ray count values subjected to a beam hardening phenomenon when the X-rays are transmitted through the object; and
attenuation amount processing means processing by applying the correcting information, prepared by the preprocessing means, to the X-ray count values for the beam hardening correction at each of the pixel areas to finally decide the X-ray attenuation amounts and processing the decided X-ray attenuation amounts.

26. The X-ray apparatus of claim 25, wherein the attenuation amount processing means comprises:
X-ray image producing means producing a photon counting X-ray image based on the X-ray attenuation amounts corrected and finally decided by correction means; and
X-ray image presenting means presenting the produced X-ray image.

27. The X-ray apparatus of claim 25, wherein
the X-ray apparatus is an X-ray medical diagnosis apparatus or an X-ray non-destructive inspection apparatus, both of which is provided with a configuration of detecting the X-rays in a photon counting system.

28. A computer-readable non-transitory recording medium storing therein a program which enables the commuter to read the program, the computer operating on the program, the computer processing data of count values, the count values being provided by radiating beam-formed X-rays having a continuous X-ray spectrum to an object, detecting the X-rays transmitted through the object, and counting, as the count values, photons of the X-rays in each of two or more preset X-ray energy bins and in each of pixel areas each consisting of one or more pixels, the computer comprising:

a calculation step calculating, in each of the X-ray energy bins and at each of the pixel areas, count data indicated by a ratio between the count values obtained with no object and with the object;

a correction step performing beam hardening correction with the count data at each of the pixel areas and in each of the X-ray energy bins to obtain X-ray attenuation amounts ($\mu t$: $\mu$ denotes a linear attenuation coefficient and t denotes a thickness of the object in a projection direction of the X-rays in the object), based on correcting information according to a preset effective atomic number, the beam hardening correction correcting a beam hardening phenomenon caused when the X-rays are transmitted through the object;

a normalization step normalizing the X-ray attenuation amounts in each of two of the X-ray energy bins, selected from the two or more X-ray energy bins, to obtain, at each of the pixel areas, at least one normalized X-ray attenuation amounts;

an estimation step estimating at least one effective atomic number from reference information showing a theoretical correspondence relationship between the normalized X-ray attenuation amounts and an effective atomic number of an element; and an equality determining step determining whether or not at least two effective atomic numbers are mutually compared to determine that the at least two effective atomic numbers are equal or are regarded as being equal, the at least two effective atomic numbers being designated among the at least one effective number estimated by the estimation step and the effective atomic number preset by the correction step.

* * * * *